(12) United States Patent
Rahimi et al.

(10) Patent No.: US 11,375,947 B2
(45) Date of Patent: Jul. 5, 2022

(54) DIAGNOSING AND TREATING MOVEMENT DISORDERS

(71) Applicant: MDDT Inc., London (CA)

(72) Inventors: Fariborz Rahimi, Kitchener (CA); Mandar Jog, London (CA)

(73) Assignee: MDDT Inc., London (CA)

( * ) Notice: Subject to any disclaimer, the term of this patent is extended or adjusted under 35 U.S.C. 154(b) by 700 days.

(21) Appl. No.: 16/256,313

(22) Filed: Jan. 24, 2019

(65) Prior Publication Data
US 2019/0150833 A1 May 23, 2019

Related U.S. Application Data

(62) Division of application No. 14/914,591, filed as application No. PCT/CA2014/050893 on Sep. 18, 2014, now Pat. No. 10,231,665.

(Continued)

(30) Foreign Application Priority Data

Sep. 20, 2013 (WO) ................ PCT/CA2013/000804

(51) Int. Cl.
*A61B 5/00* (2006.01)
*A61B 5/11* (2006.01)
(Continued)

(52) U.S. Cl.
CPC .............. *A61B 5/4839* (2013.01); *A61B 5/11* (2013.01); *A61B 5/1101* (2013.01);
(Continued)

(58) Field of Classification Search
CPC ....... A61B 5/4839; A61B 5/11; A61B 5/1101; A61B 5/1127; A61B 5/4082;
(Continued)

(56) References Cited

U.S. PATENT DOCUMENTS

| | | | |
|---|---|---|---|
| 4,464,617 A | * | 8/1984 | Yantovsky ............. H02K 55/02 318/717 |
| 5,313,968 A | | 5/1994 | Logan et al. |

(Continued)

FOREIGN PATENT DOCUMENTS

| CA | 2781267 A1 | 5/2011 |
|---|---|---|
| JP | 2003523223 A | 8/2003 |

(Continued)

OTHER PUBLICATIONS

First Examination Report dated Apr. 29, 2020 on Indian patent application 201627008063.

(Continued)

*Primary Examiner* — Daniel L Cerioni
(74) *Attorney, Agent, or Firm* — Brunet & Co. Ltd.; Robert Brunet; Hans Koenig

(57) ABSTRACT

A system for obtaining and analyzing data for overall joint motion from a plurality of joints of a subject experiencing a movement disorder involves a plurality of kinematic sensors configured to be placed on a body of a subject proximal a plurality of joints. The kinematic sensors are selected to measure overall joint motion with sufficient degrees of freedom for individual joints so that data collected by the sensors can be deconstructed into multiple degrees of freedom for individual joints and analyzed to provide amplitude of the movements caused by the movement disorder and/or relative contributions from and/or directional bias for each muscle group that may be implicated in the movement of each joint. The system permits determining a treatment regimen based on the amplitude of the movements and/or the relative contribution and/or directional bias of each muscle group to the movements caused by the movement disorder.

11 Claims, 29 Drawing Sheets

Related U.S. Application Data

(60) Provisional application No. 61/993,489, filed on May 15, 2014.

(51) Int. Cl.

| | | |
|---|---|---|
| *A61N 2/00* | (2006.01) | |
| *A61F 5/01* | (2006.01) | |
| *A61M 5/172* | (2006.01) | |
| *A61N 1/36* | (2006.01) | |
| *A61K 38/48* | (2006.01) | |
| *A61N 5/06* | (2006.01) | |
| *A61N 7/00* | (2006.01) | |
| *A61H 23/02* | (2006.01) | |
| *A61H 39/08* | (2006.01) | |

(52) U.S. Cl.
CPC .......... *A61B 5/1127* (2013.01); *A61B 5/4082* (2013.01); *A61B 5/4519* (2013.01); *A61B 5/4848* (2013.01); *A61F 5/01* (2013.01); *A61K 38/4893* (2013.01); *A61M 5/1723* (2013.01); *A61N 1/36067* (2013.01); *A61N 2/002* (2013.01); *A61N 2/006* (2013.01); *A61N 5/0613* (2013.01); *A61B 2562/0219* (2013.01); *A61B 2562/0223* (2013.01); *A61H 23/0245* (2013.01); *A61H 39/08* (2013.01); *A61H 2201/10* (2013.01); *A61H 2201/5058* (2013.01); *A61H 2201/5061* (2013.01); *A61H 2201/5069* (2013.01); *A61H 2201/5084* (2013.01); *A61H 2201/5092* (2013.01); *A61H 2230/60* (2013.01); *A61H 2230/62* (2013.01); *A61N 7/00* (2013.01)

(58) Field of Classification Search
CPC ....... A61B 5/4519; A61B 5/4848; A61F 5/01; A61K 38/4893; A61M 5/1723; A61N 1/36067; A61N 2/002; A61N 2/006; A61N 5/0613

See application file for complete search history.

(56) References Cited

U.S. PATENT DOCUMENTS

| | | | |
|---|---|---|---|
| 5,832,932 A | 11/1998 | Elsberry et al. | |
| 7,981,052 B2 | 7/2011 | Akay | |
| 2008/0279896 A1 | 11/2008 | Heinen et al. | |
| 2010/0030119 A1 | 2/2010 | McNames et al. | |
| 2011/0256983 A1* | 10/2011 | Malack .............. | A63B 23/0405 482/4 |
| 2011/0289147 A1* | 11/2011 | Styles ................... | G06F 1/1613 709/205 |
| 2012/0053126 A1 | 3/2012 | Turkel et al. | |
| 2012/0083700 A1* | 4/2012 | Osorio ..................... | A61B 5/11 600/483 |
| 2012/0219418 A1* | 8/2012 | Ingerslew ............... | F03D 17/00 416/1 |
| 2013/0017807 A1* | 1/2013 | Rooyen ................... | H04W 4/18 455/414.1 |
| 2013/0131555 A1* | 5/2013 | Hook ................... | A61B 5/0022 600/595 |

FOREIGN PATENT DOCUMENTS

| | | |
|---|---|---|
| JP | 2008245917 A | 10/2008 |
| KR | 20090027732 A | 3/2009 |
| KR | 20110012119 A | 2/2011 |
| WO | 01/07112 A2 | 2/2001 |

OTHER PUBLICATIONS

Rahimi et al., Tremor Suppression Orthoses for Parkinson's Patients: A Frequency Range Perspective, 31st Annual International Conference of the IEEE EMBS Minneapolis, Minnesota, USA, Sep. 2-6, 2009, pp. 1565-1568.
Rahimi et al., Capturing Whole-Body Mobility of Patients with Parkinson Disease Using Inertial Motion Sensors: Expected Challenges and Rewards, 33rd Annual International Conference of the IEEE EMBS Boston, Massachusetts USA, Aug. 30-Sep. 3, 2011, pp. 5833-5838.
Rahimi et al., Variability of Hand Tremor in Rest and in Posture—A Pilot Study, 33rd Annual International Conference of the IEEE EMBS Boston, Massachusetts USA, Aug. 30- Sep. 3, 2011, pp. 470-473.
Rahimi et al., Effectiveness of BoNT A in Parkinson's Disease Upper Limb Tremor Management, The Canadian Journal of Neurological Sciences, 2013; 40: pp. 663-669.
Rahimi et al., Using Ecological Whole Body Kinematics to Evaluate Effects of Medication Adjustment in Parkinson Disease, Journal of Parkinson's Disease 4 (2014) pp. 617-627.
International Search Report and Written Opinion on PCT/CA2014/050893 dated Dec. 22, 2014.
Office action dated Mar. 23, 2018 on Chinese Patent Application 201480063793.X.
Office action dated Aug. 21, 2018 on Japanese Patent Application 2016-543277.
Extended-European-Search-Report dated Sep. 25, 2017 for EP 14845085.1.
Office action dated May 17, 2018 on U.S. Appl. No. 14/914,591.
Office Action dated Jan. 12, 2020 on Japanese application 2019-045441.
Office Action dated Feb. 19, 2019 on European application 14845085.1.
Office Action dated Nov. 1, 2018 on Australian application 2014324018.
Office Action dated Mar. 5, 2019 on Australian application 2014324018.
First Grounds for Rejection dated Nov. 19, 2020 on Korean patent application 10-2016-7009719.

\* cited by examiner

RMS* = Root Mean Squared

Data Sheet: Essential Tremor - Left

| | Wrist - Angular RMS Amplitude | | | | Shoulder - Angular RMS Amplitude | | | Elbow - Angular RMS Amplitude |
|---|---|---|---|---|---|---|---|---|
| | Total Amplitude | % Flx/Ext | % Rad/Uln | % Pro/Sup | Total Amplitude | % Flx/Ext | % Abd/Add | Total Amplitude |
| Posture-1 | 1.65 | 68.1 | 17.3 | 14.6 | 0.30 | 38.9 | 61.1 | 0.21 |
| Posture-2 | 2.26 | 68.1 | 24.5 | 7.5 | 0.29 | 27.3 | 72.7 | 0.22 |
| Load-1 | 2.04 | 34.0 | 35.6 | 30.4 | 0.26 | 74.3 | 25.7 | 0.62 |
| Load-2 | 1.12 | 27.6 | 35.3 | 37.1 | 0.34 | 59.4 | 40.6 | 0.67 |

| Wrist Bias | | |
|---|---|---|
| | Posture-1 | Posture-2 |
| Posture-2 Fls-Ext | Rad-Uln | Prn-Sup |
| 6 | 13 | 12 |

Fig. 11A 1.1 When selecting an assessment task with the maximum tremor amplitude, pick a task within the inclusion criteria max/min amplitude values. If maximum task has tremor value above the inclusion criteria select the next highest task that is within inclusion max/min range.

1.2 If 2 or more tasks have the same total tremor amplitude value, choose the task with the higher variability.

2.1 From kinematic data for Angular RMS Amplitude in Fig. 11A, write WRIST total tremor amplitude (°) for each assessment task.

2.2 Determine assessment task with largest tremor amplitude and compare this amplitude value to the wrist dosing table below.

| WRIST Amplitude (°) | Max Dose (U) |
|---|---|
| > 4.06 | 160 |
| 3.48 – 4.05 | 140 |
| 2.90 – 3.47 | 120 |
| 2.33 – 2.89 | 100 |
| 1.75 – 2.32 | 80 |
| 1.17 – 1.74 | 60 |
| 0.51 – 1.16 | 40 |
| 0.20 – 0.50 | 30 |

3.1 Write total WRIST dose using the table above determined in STEP 2.2.
i.e. Posture-2 total amplitude is the highest at 2.26°, which corresponds to 80 U in the table above

WRIST Tremor Amplitude

| Assessment task | Total Tremor Amplitude (°) (STEP 2.1) |
|---|---|
| Posture-1 | 1.65 |
| Posture-2 | 2.26 |
| Load-1 | 2.04 |
| Load-2 | 1.12 |
| Total WRIST Dosage (U) (STEP 3.1) | 80 |

Fig. 11B

Allocate WRIST total dose by directional contribution

| Degree of Freedom | % Cont. (STEP 4.1) | DOF Dose (U) (STEP 4.2) |
|---|---|---|
| Flexion-Extension | 67 | = %F/E x Total W. Dose<br>68.1% x 80 U = 54.5 U |
| Radial-Ulnar | 23 | = %R/U x Total W. Dose<br>24.5% x 80 U = 19.6 U |
| Pronation-Supination | 10 | = %P/S x Total W. Dose<br>7.5% x 80 U = 6.0 U |
| Total WRIST dose (R/U + F/E + P/S ) (U)<br>(STEP 3.1) | | 80 |

STEP 4

4.1 Write down the % contribution for each degree of freedom (DOF) for the task with the largest tremor amplitude, calculated from the kinematic data for Angular RMS Amplitude in Fig. 11A.
*i.e. for Posture-2*

4.2 Multiply "% contribution" for each degree of freedom (STEP 4.1) by "total WRIST dosage" (STEP 3.1) to determine "DOF Dose".
*i.e. R/U dose = 80 U x 24.5% = 19.6 U*

4.3 Do not Round values to the nearest 5. Keep as exact as possible. Rounding of units will be done at the very end of wrist calculations.

Fig. 11C

Determine direction and magnitude of WRIST bias

| Degree of Freedom | Degree of Deviation (°) (STEP 5.1) | Deviation from Expected DOF bias (°) (STEP 5.2) | Direction of Deviation (STEP 5.3) | Direction in Dose Change (U) (STEP 5.4) |
|---|---|---|---|---|
| Flexion-Extension (Posture-2) | +6 | = degree of deviation - (-0) <br> 6 – (0) = +6 | (Flexion (+)) | +5 U |
|  |  |  | Extension (-) | -5 U |
| Radial-Ulnar (Posture-1) | +13 | = degree of deviation - (15) <br> 13 – (-15) = +28 | (Radial (+)) | +10 U |
|  |  |  | Ulnar (-) | -10 U |
| Pronation-Supination (Posture-2) | +12 | = degree of deviation - (0) <br> 12- (0) = +12 | (Pronation (+)) | +5 U |
|  |  |  | Supination (-) | -5 U |

The direction of deviation that is circled is given the additional Units of drug 5.1 From the kinematic data for Wrist Bias in Fig. 11A, write degree of deviation for each Degree of Freedom (DOF).

5.2 Subtract "degree of deviation" *(STEP 5.1)* from "deviation from expected DOF bias", using formulas above.
 *i.e. R/U deviation was +13 ° from x-axis thus, = (+13 °) - (-15 °) = + 28°*

5.3 Circle which direction the deviation favours. The direction of deviation is determined by the + / - value after calculation.
 *i.e. R/U deviation was + 28°, thus this positive value means radial bias*

5.4 Compare the "deviation from expected bias" *(STEP 5.2)* to the "deviation from expected range" table *(right)*.

| Deviation from Expected Range (°) | Dose Change (U) (STEP 5.4) |
|---|---|
| \|0 to 5\| | 0 |
| \|6 to 15\| | 5 |
| \|≥16\| | 10 |

STEP 5

Fig. 11D

Determine WRIST dosing by degree of freedom

| Degree of Freedom | DOF Dose with Bias (U) *(STEP 5.5)* | |
|---|---|---|
| | Flexion<br>= [(STEP 4.2)/2] ± (STEP 5.4)<br><br>54.5/2 + 5 = 32.25 U | Extension<br>= [(STEP 4.2)/2] ± (STEP 5.4)<br><br>54.5/2 - 5 = 22.25 |
| Flexion-Extension<br>(Posture-2) | | |
| Radial-Ulnar<br>(Posture-1) | Radial<br>= [(STEP 4.2)/2] ± (STEP 5.4)<br><br>19.6/2 + 10 = 19.8 U | Ulnar<br>= [(STEP 4.2)/2] ± (STEP 5.4)<br><br>19.6/2 - 10 = -0.2 ---> 0 U |
| Pronation-Supination<br>(Post-2) | Pronation<br>= [(STEP 4.2)/2] ± (STEP 5.4)<br><br>6.0/2 + 5 = 8 U | Supination<br>= [(STEP 4.2)/2] ± (STEP 5.4)<br><br>6.0/2 - 5 = -2 ---> 0 U |

STEP 5

5.5 *Using the total dose for each DOF from STEP 4.2 (Fig. 11C) and the dose change for directional bias determined in STEP 5.4 (Fig. 11D), calculate "DOF dose with bias".*

5.6 *If final value is less then 0 (i.e. -1) round to 0*

Fig. 11E

Determine Injection Dose for WRIST muscles

| WRIST muscles | Exact Dose per Muscle (U) *(STEP 6.1)* | Final Dose per Muscle (U) *(STEP 6.2)* |
|---|---|---|
| FCR | = Flexion/2 + Radial/2 | 32.25/2 + 19.8/2 = 26.025 | 25 |
| FCU | = Flexion/2 + Ulnar/2 | 32.25/2 + 0/2 = 16.125 | 15 |
| ECR | = Extension/2 + Radial/2 | 22.25/2 + 19.8/2 = 21.15 | 20 |
| ECU | = Extension/2 + Ulnar/2 | 22.25/2 + 0/2 = 11.125 | 10 |
| PT | = Pronation/2 | 8/2 = 4 | 5 |
| PQ | = Pronation/2 | 8/2 = 4 | 5 |
| Supinator | = Supination | 0 | 0 |
| | Total WRIST Dosage (U) *(STEP 3.1)* | 80 |

6.1 Calculate "exact dose per muscle" by using *STEP 5.5* doses and the above formulas
6.2 To simplify injections, round *STEP 5.5* dosages by multiple of 5 to determine "Final Dose per muscle".
   *i.e. If values between 0.1 to 2.4 round to 0*
      *between 2.5 to 4.9 round to 5*
      *between 5.1 to 7.4 round to 5*
      *between 7.5 to 9.9 round to 10*
   This rounding principle applies to all joints and favors under-dosing.
6.3 Total all the "Final Dose per muscle" units and ensure the values do not exceed maximum total WRIST dosage *(STEP 3.1)*.
6.4 If 5 U needs to be removed, decrease dose allocated to the ECR muscle first to minimize risk of toxin spread; if 10 U needs to be removed, decrease an additional 5 U from ECU as well.
   If total rounding results in under-dosing (< total W dosage), this is considered acceptable.

STEP 6 ⇧

Fig. 11F

Determine Injection Dosing for ELBOW muscles

| ELBOW Assessment task | Amplitude (°) |
|---|---|
| Posture-1 | 0.21 |
| Posture-2 | 0.22 |
| Load-1 | 0.62 |
| Load-2 | 0.67 |
| Total ELBOW dose (U) (STEP 7.3) | 50 |

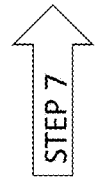

STEP 7

7.1 From kinematic data for Angular RMS Amplitude in Fig. 11A, write ELBOW total tremor amplitude (°) for each assessment task.

7.2 Determine assessment task with largest tremor amplitude and compare value to the elbow dosing table below.

| Elbow Amplitude (°) | Dose (U) |
|---|---|
| > 1.75 | 100 |
| 1.48 – 1.74 | 80 |
| 1.21 – 1.47 | 70 |
| 0.93 – 1.20 | 60 |
| 0.66 – 0.92 | 50 |
| 0.38 – 0.65 | 40 |
| 0.1 – 0.37 | 30 |

7.3 Write total ELBOW dose using the table above.
*i.e. Load-2 with 0.67° indicates a 50 U dose*

Injection Dose for ELBOW muscles

| ELBOW muscles | Final Dose per Muscle (U) (STEP 8.1) |
|---|---|
| Biceps | = Total E. Dose (STEP 7.3) ÷ 2<br>50/2 = 25 |
| Triceps | = Total E. Dose (STEP 7.3) ÷ 2<br>50/2 = 25 |
| Total ELBOW dose (U) (Biceps + Triceps) (STEP 7.3) | 50 |

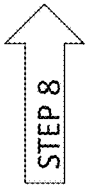

STEP 8

8.1 Using STEP 7.3 total ELBOW dose, divide this value by 2.
*i.e. Load-2 with 50 U ÷ 2 = 25 U, therefore Biceps get 25 U and Triceps get 25 U*

Fig. 11G

Determine Injection Dosing for SHOULDER muscles

| SHOULDER Assessment task | Amplitude (°) *(STEP 9.1)* |
|---|---|
| Posture-1 | 0.30 |
| Posture-2 | 0.29 |
| Load-1 | 0.26 |
| Load-2 | 0.34 |
| Total SHOULDER dose (U) *(STEP 9.3)* | 60 |

9.1 From the kinematic data for Angular RMS Amplitude in Fig. 11A, write SHOULDER total tremor amplitude (°) for each assessment task.
9.2 Determine assessment task with largest tremor amplitude and compare value to the shoulder dosing table below.

| SHOULDER Amplitude (°) | Dose (U) |
|---|---|
| > 1.13 | 140 |
| 0.92 – 1.12 | 120 |
| 0.71 – 0.91 | 100 |
| 0.50 – 0.70 | 80 |
| 0.29 – 0.49 | 60 |
| 0.1 – 0.28 | 40 |

9.3 Write total SHOULDER dose using the table above.
*i.e. Load-2 with 0.34° indicates a 60 U dose*

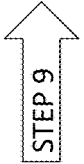
STEP 9

Allocate SHOULDER total dose by directional contribution

| Degree of Freedom | % Contribution *(STEP 10.1)* | Dose (U) *(STEP 10.2)* | Dose per DOF breakdown (U) *(STEP 11.1)* |
|---|---|---|---|
| Flexion-Extension | 59.4 | = % F/E *(STEP 10.1)* × Total S. Dose *(STEP 9.3)* <br> 59.4% × 60 U = 35.64 U | Flexion <br> = F/E dose ÷ 2 <br> 35.64/2 = 17.82 U <br><br> Extension <br> = F/E dose ÷ 2 <br> 35.64/2 = 17.82 U |
| Abduction-Adduction | 40.6 | = % Abd/Add *(STEP 10.1)* × Total S. Dose *(STEP 9.3)* <br> 40.6% × 60 U = 24.36 U | Abduction <br> = Abd/Add dose ÷ 2 <br> 24.36/2 = 12.18 U <br><br> Adduction <br> = Abd/Add dose ÷ 2 <br> 24.36/2 = 12.18 U |
| Total SHOULDER dose (U) (F + E + Abd + Add) *(STEP 9.3)* | | | 60 |

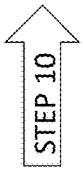 10.1 Using the assessment task with the largest tremor amplitude, write down the % contribution for each degree of freedom (DOF) from the kinematic data in Fig. 11A. *i.e. % F/E = 59.4%; % A/A = 40.6%*
10.2 Multiply % contribution for each degree of freedom *(STEP 10.1)* by total SHOULDER dose *(from STEP 9.3)* to determine dose per DOF.

 11.1 Divide *STEP 10.2* dose by 2 to calculate the dose per DOF breakdown.

STEP 10

STEP 11

Fig. 11H

Injection Dose for SHOULDER muscles

| SHOULDER Muscles | Exact Dose per Muscle (U) *(STEP 12.1)* | Final Dose per Muscle (U) *(STEP 12.2)* |
|---|---|---|
| Pec. Maj. | Flexion + Adduction<br>17.82 + 12.18 = 30 | 30 |
| Teres Maj. | Extension<br>17.82 | 20 |
| M. Delt. | Abduction ÷ 2<br>12.18/2 = 6.09 | 5 |
| M. Supras. | Abduction ÷ 2<br>12.18/2 = 6.09 | 5 |
| Total SHOULDER Dosage (U) *(STEP 9.3)* | | 60 |

STEP 12 ⇧

12.1 Using *STEP 11.1* dosages and the formulas above, calculate "exact dose per muscle" dosages for each SHOULDER muscle.

12.2 To simplify injections, round "exact dose per muscle" dosages by increments of 5 U to determine "Final Dose per muscle".

12.3 The final dosages should not exceed total SHOULDER dose *(STEP 9.3)*.

12.4 If dose for M Delt and M Supras is 5, then give M Supras 10 U and M Delt 0 U.

12.5 If total rounding results in under-dosing (< total S dosage), this is considered acceptable. However, if rounding results in over-dosing, remove 5 U from Pec. Maj.

Fig. 11I

Injection Dose SUMMARY SHEET

| WRIST muscles | Final Dose per Muscle (U) *(STEP 6.2)* |
|---|---|
| FCR | 25 |
| FCU | 15 |
| ECR | 20 |
| ECU | 10 |
| PT | 5 |
| PQ | 5 |
| Supinator | 0 |
| Total WRIST Dosage (U) *(STEP 3.1)* | 80 |

| ELBOW muscles | Final Dose per Muscle (U) *(STEP 8.1)* |
|---|---|
| Biceps | 25 |
| Triceps | 25 |
| Total ELBOW dose (U) *(STEP 7.3)* | 50 |

| SHOULDER Muscles | Final Dose per Muscle (U) *(STEP 12.2)* |
|---|---|
| Pec. Maj. | 30 |
| Teres Maj. | 20 |
| M. Delt. | 5 |
| M. Supras. | 5 |
| Total SHOULDER Dosage (U) *(STEP 9.3)* | 60 |

Total ARM Dose (U) = Total WRIST + ELBOW + SHOULDER Dosages
190

Fig. 11J

DIAGNOSING AND TREATING MOVEMENT DISORDERS

CROSS-REFERENCE TO RELATED APPLICATIONS

This application is a divisional of U.S. patent application Ser. No. 14/914,591 filed Feb. 25, 2016, which is a national entry of International Patent Application PCT/CA2014/050893 filed Sep. 18, 2014, which further claimed the benefit of U.S. Provisional Patent application Ser. No. 61/993,489 filed May 15, 2014 and priority to International Patent Application PCT/CA2013/000804 filed Sep. 20, 2013.

FIELD OF THE INVENTION

The present invention relates medicine, particularly to methods and systems for diagnosing and treating movement disorders.

BACKGROUND OF THE INVENTION

Tremor is a relatively treatment-resistant symptom of various movement disorders, for example Parkinson's disease (PD) and Essential Tremor (ET), and Essential Tremor is one of the most common movement disorders. Tremor is assumed to be visually easy to assess and therefore should be relatively easy to treat ET action tremors (postural or kinetic) and PD rest tremors. However, detailed kinematic assessment of both tremor types to deconstruct tremor dynamics, including both muscle composition and directional bias have not been done to validate these assumptions.

Although tremor in ET and PD can involve the head, face, and tongue, the most common site remains the limbs, particularly the upper limbs. Subsequent functional impairment is a result of tremor, and this can be substantially disabling if the dominant arm is affected. In PD, tremor symptoms are commonly one-sided while for ET the tremor will be bilateral. In addition, the presence of tremor is an obvious visible symptom, which can be cosmetically disabling, making patients feel as though they "stand out" causing emotionally distress. Due to such functional and psychological disability, an effective treatment method for focal tremor remains an important need in affected individuals. While options exist for management of ET and PD tremor, the therapeutic efficacy can still be quite poor with the side effects of medication and danger in brain surgery pose considerable risk, especially in the older age group.

Botulinum neurotoxin such as type A or B (BoNT A, BoNT B, BTX-A, BTX-B) injection therapy has shown efficacy and is indicated for the management of focal disorders such as cervical dystonia (torticollis), blepharospasm and upper limb spasticity, to name a few. Although tremor has been treated with BoNT A, the studies have been open-label, or small and the results of BoNT A have not generally been particularly favorable. For ET, injection with BoNT A can indeed reduce postural tremor amplitude as measured by accelerometry and clinical rating scales. However, all patients had some degree of weakness as a side effect, and functional disability and action tremor did not improve significantly. It is possible that despite the reduction in tremor, weakness overshadowed the improvement and resulted in a lack of significant functional improvement seen. Nevertheless, chemodenervation with BoNT A appears to be a viable option for treatment of ET. However, this has not been largely accepted as a primary treatment option by clinicians, approved by health regulatory bodies, nor is it reimbursed by insurance companies for off-label use.

The lack of functional improvement using BoNT A is a side effect profile produced by the injection. Intramuscular injections can produce substantial weakness in the muscles due to the toxin's well-known action. This weakness is in the muscles injected and also in the adjacent muscles due to the spread of the toxin. It is known that this weakness and spread is dose and volume dependent. However, the most significant determinant of this side effect may be the selection of the appropriate and most responsible muscles that contribute to the tremor seen and the dosage injected within the muscles, and not to inject non-contributing muscles. The most important component of muscle selection is the clinician's ability to determine the predominant direction of movement of the affected body part. This is true even for dystonia and spasticity, the two other syndromes where BoNT A is successfully used. In these conditions, the movement can be generally fairly stereotyped and the predominant postures of the body parts affected can be visually assessed by the clinician. However, when tremor is superimposed on say cervical dystonia, the assessment of the movement and the subsequent injection pattern determination becomes that much more difficult.

To date, the tremor of PD and ET have been assumed to having well established "clinical features": rest tremor in PD and postural and kinetic tremor in ET. Additionally, the predominant composition of these tremor types has been also assumed to be flexion/extension, mainly present at the wrist. Finally, despite the complexity of such tremors, the judgment of which muscles to inject and the dosage of BoNT A required is achieved purely on visual inspection, different for each patient. Tremor in the upper limb can be complex to assess visually simply because of the number of body parts involved. Traditionally tremor has been associated at the wrist joint and fingers, however, our findings show the tremors are present often at the shoulder, elbow, wrist, and in fingers. In addition, each of these joints has many degrees of freedom in terms of movement. The wrist can flex and extend, and show ulnar and radial deviation, while at the same time the elbow may show pronation-supination and flexion-extension. The shoulder can also flex-extend and have abduction-adduction movements. Such multidimensional motion is then summed in producing the actual tremor. The clinician has to then visually decompose these components and then determine the relative contributions of each in order to estimate which muscle groups to select for injection. In most cases this is a very difficult task and may over- or under-estimate the movement subcomponents. If this happens, the injections of BoNT A may be given in incorrect muscle groups resulting in suboptimal benefit and increased side effects.

Thus, there is a need in the art for methods that better assess tremor composition.

SUMMARY OF THE INVENTION

In one aspect of the invention, there is provided a system for obtaining and analyzing data for overall joint motion from a plurality of joints of a subject experiencing a movement disorder, the system comprising: a plurality of kinematic sensors configured to be placed on a body of a subject experiencing a movement disorder proximal a plurality of joints of the subject, the kinematic sensors selected to measure overall joint motion with sufficient degrees of freedom for individual joints so that data collected by the sensors can be deconstructed into multiple degrees of freedom for individual joints and analyzed to provide amplitude of the movements caused by the movement disorder, and relative contributions from and directional bias for each muscle group that may be implicated in the movement of each joint; and, a non-transient, physical memory device configured to accept data collected by the kinematic sensors and having computer executable instructions stored thereon to deconstruct the data collected by the sensors for overall joint motion into multiple degrees of freedom for individual joints and analyzing the multiple degrees of freedom for the amplitude of the movements caused by the movement disorder and the relative contributions from and directional bias for each muscle group that may be implicated in the movement of each joint.

In another aspect of the invention, there is provided a method of determining muscle groups involved in a movement disorder in a subject, the method comprising deconstructing sensor data for overall joint motion collected from a plurality of joints of a subject experiencing a movement disorder into multiple degrees of freedom for individual joints and analyzing the multiple degrees of freedom for relative contributions from and directional bias for each muscle group that may be implicated in the movement of each joint, the deconstructing and/or analyzing accomplished by computer executable instructions therefor stored in a non-transient, physical memory device.

In another aspect of the invention, there is provided a method of determining a treatment regimen for treating a movement disorder in a subject, the method comprising:

determining amplitude and muscle composition of movements of a subject caused by a movement disorder by deconstructing sensor data for overall joint motion collected from a plurality of joints of a subject into multiple degrees of freedom for individual joints and analyzing the multiple degrees of freedom for amplitude of the movements caused by the movement disorder and for relative contributions from each muscle group that may be involved in the movement of each joint caused by the movement disorder, the deconstructing and/or analyzing accomplished by computer executable instructions therefor stored in a non-transient, physical memory device; and, determining a personalized treatment regimen for the subject from the amplitude and relative contribution of each muscle group to the movements caused by the movement disorder.

In another aspect of the invention, there is provided a method of treating a subject with a movement disorder, the method comprising: determining amplitude and muscle composition of movements of a subject caused by a movement disorder by deconstructing sensor data for overall joint motion collected from a plurality of joints of a subject into multiple degrees of freedom for individual joints and analyzing the multiple degrees of freedom for amplitude of the movements caused by the movement disorder and for relative contributions from each muscle group that may be involved in the movement of each joint caused by the movement disorder; and, administering to the subject a personalized treatment regimen determined from the amplitude and relative contribution of each muscle group to the movements caused by the movement disorder.

In another aspect of the invention, there is provided a system for providing a dosage recommendation for treating a movement disorder with a drug in a subject, the system comprising: a plurality of kinematic sensors configured to be placed on a body of a subject experiencing a movement disorder proximal a plurality of joints of the subject, the kinematic sensors selected to measure overall joint motion with sufficient degrees of freedom for individual joints so that data collected by the sensors can be deconstructed into multiple degrees of freedom for individual joints and analyzed to provide amplitude of the movements caused by the movement disorder, and relative contributions from and directional bias for each muscle group that may be implicated in the movement of each joint; and, a non-transient, physical memory device configured to accept data collected by the kinematic sensors and having computer executable instructions stored thereon to deconstruct the data collected by the sensors for overall joint motion into multiple degrees of freedom for individual joints and analyzing the multiple degrees of freedom for the amplitude of the movements caused by the movement disorder and the relative contributions from and directional bias for each muscle group that may be implicated in the movement of each joint, wherein for a given joint, the computer executable instructions: further determine from the amplitude of the movements a total dosage of the drug to administer to the muscles implicated in the movements at the joint; further determine from the relative contributions of each muscle group a proportion of the total dosage to administer to each muscle group implicated in the movements at the joint; further determine from the directional bias a proportion of the dosage to be administered to each muscle group to administer to each individual muscle in the muscle group; and, calculate from the total dosage and each determined proportion the dosage of the drug to administer to each individual muscle implicated in the movement of the joint.

In another aspect of the invention, there is provided a method for providing a dosage recommendation for treating a movement disorder with a drug, the method comprising: deconstructing sensor data for overall joint motion collected from a plurality of joints of a subject experiencing a movement disorder into multiple degrees of freedom for individual joints and analyzing the multiple degrees of freedom for relative contributions from and directional bias for each muscle group that may be implicated in the movement of each joint; determining from amplitude of the movement at a given joint a total dosage of the drug to administer to muscles implicated in the movements at the given joint; determining from the relative contributions of each muscle group a proportion of the total dosage to administer to each muscle group implicated in the movements at the given joint; determining from the directional bias a proportion of the dosage to be administered to each muscle group to administer to each individual muscle in the muscle group; and, calculating from the total dosage and each determined proportion the dosage of the drug to administer to each individual muscle implicated in the movement of the joint.

Movement disorders involve the involuntary movement of body segments. It has now been found that any given involuntary movement may comprise contributions from any number of muscles, including muscles distal from the body segment affected by the involuntary movement. Therefore, in the present invention, a plurality of kinematic sensors are placed proximal a plurality of joints and used to measure overall joint motion with sufficient degrees of freedom for individual joints so that data collected by the sensors can be deconstructed into multiple degrees of freedom for individual joints and analyzed to provide relative contributions from each muscle group that may be implicated in the movement of each joint. The analysis also preferably provides directional bias for the muscle groups implicated in the movement of each joint. In this way, the actual muscle group composition, and preferably the directional bias within the muscle group as well, for any given abnormal movement can be determined, and a therapy developed to specifically target the muscle groups involved in that abnormal movement.

Movement disorders include, for example, tremor (e.g. Parkinson's disease (PD), essential tremor (ET), writing tremor), dystonia (e.g. torticollis or cervical dystonia (CD), task-specific writing dystonia), ataxia, chorea, myoclonus, ballismus, dysmetria, postural disorders, spasticity (e.g. focal spasticity from stroke, upper limb spasticity), blepharospasm, multiple sclerosis and cerebral palsy. Of particular interest are Parkinson's disease (PD) and essential tremor (ET). Movements involving muscle groups from any part of the body may be measured and analyzed, for example muscles that control motion around joints of the lower part of the body (e.g. hips, knees, ankles and toes) or around joints of the upper part of the body (e.g. neck, shoulders, elbows, wrists and fingers). Because of the spinal column, the neck may comprise a plurality of joints and measurements made at the neck may be considered to involve measuring motion at a plurality joints. Some examples of muscle groups whose contribution to the abnormal movement may be determined include but are not limited to lateral shift/tilt, saggital shift/tilt, axial rotation, outward/inward medial rotation, retraction/protraction and inversion/eversion muscle groups, as well as flexion-extensor (F/E), ulnar-radial (U/R), pronation-supination (P/S) and abduction-adduction (A/A) muscles. For abnormal movements of upper limbs and neck, the muscle groups of greatest importance may be one or more of lateral shift/tilt related muscles, saggital shift/tilt related muscles, axial rotation neck muscles, flexion-extensor (F/E) muscles, ulnar-radial (U/R) muscles, pronation-supination (P/S) muscles and abduction-adduction (A/A) muscles. Some examples of specific muscles include flexor carpi radialis, flexor carpi ulnaris, brachioradialis, extensor carpi radialis, extensor carpi ulnaris, pronator teres, pronator quadratus, supinator, biceps, pectoralis, teres major, triceps, deltoids, supraspinatus, infraspinatus, semispinalis capitis, splenius capitis, trapezius, levator scapulae, sternocleidomastoid, scalene muscles, splenius cervicalis, and longissimus capitis. Of particular interest are joints and muscle groups of the upper body, particularly especially the upper limbs and neck.

Kinematic sensors include any device that can determine direction of motion of a body segment. The sensors may be kinematically connected to the body segment or may track the body segment without being connected thereto. Kinematic sensors may include, for example, one or more of a transducer, inclinometer, electromagnetometer, potentiometer, camera-based visible light tracking, camera-based IR-tracking, proximity sensor, strain gauge, magnetic or electromagnetic tracker, inertial sensor, accelerometer, gyroscope, surface EMG, torsiometer (e.g. electro-torsiometer), goniometer (e.g. electro-goniometer), load cell sensor or full body inertial measurement unit. Kinematic sensors may be kinematically connected to a subject by, for example, direct attachment to the subject's body segment or attachment to an article of clothing, jewelry or the like. The sensors could be built into a body suit (e.g. an inertial measurement unit) worn by the subject. Kinematic sensors that do not require attachment to the body segment may be positioned in line-of-sight of the body segment.

There should be a sufficient number of kinematic sensors to measure overall joint motion with sufficient degrees of freedom for individual joints so that data collected by the sensors can be deconstructed into multiple degrees of freedom for individual joints and analyzed to provide relative contributions from and directional bias for each muscle group that may be implicated in the movement of each joint. The number of kinematic sensors required depends on the type of sensor used, the number of joints being measured and the placement of the sensors on the subject's body segments. Sensors capable of detecting motion with more than one degree of freedom and/or detecting motion at a specific joint independent of motion from other body segments are particularly useful, for example goniometers or torsiometers, although in practice a plurality of types of kinematic sensors may be used. For example, a torsiometer placed diagonally across the subject's wrist provides better measurement of wrist motion than an inclinometer placed on a dorsal surface of a hand. A plurality of different types of sensors may be used to compensate for the shortcomings of any one type of sensor; for example, if one sensor type has less than three degrees of freedom, then other sensor types may be desired. However, using only one sensor type is possible if that sensor type has at least three degrees of freedom. Data may be transmitted from the sensors through wired connections or wirelessly.

It is possible to compile data representing the motion along a sufficient number of degrees of freedom for each joint by placing sensors at a plurality of joints and measuring the motion at each joint independently along a desired number of degrees of freedom (e.g. three degrees of freedom) around that joint. Because any given abnormal movement may comprise a contribution from any number of muscles, such measurement of motion around each of the joints that may be implicated in the abnormal movement permits decomposition of the sensor data into the particular motions, and therefore the particular joints, muscle group composition and directional bias, involved in a single abnormal movement. The distribution of composition among joints (e.g. fingers, wrist, elbow, shoulder neck, etc.), the muscle group composition (e.g. F/E, U/R, P/S, A/A) and the directional bias within each joint muscle group provides information to determine the individual muscles involved in and their respective contributions to the abnormal movement. This permits accurate targeting of the muscles for therapy for the abnormal movement in question. Thus, therapy may be based on relative contribution of each muscle to the abnormal movement, the contribution of each muscle being determined from the analyzed sensor data showing the muscle group composition for the movement and the directional bias within each of the muscle groups that are part of the composition.

The analysis of sensor data may be embodied in a computer program or software. The software may have the capability of simultaneously recording and analyzing body movements and recognizing what abnormal movements are. Or, body movement data may be collected first, followed by analysis by the software. The software may be able to detect, for example, tremor movements as well as abnormal postures (e.g. asymmetry in neck position) found at limb joints (e.g. wrist, elbow, shoulder, neck, ankle and knee). The software filters and analyzes the raw sensor data related to motions at each joint into clinically relevant information, e.g. muscle composition and directional bias. This may be done following an assessment conducted by medical staff with hardware sensors for recording the movement disorder from the patient. The software may summarize the values collected for each channel of sensor signal after calibration and assessment. Signal processing and filtered band-pass may also be applied to the recorded signal along with the data during assessment, which may be compared to values from the calibration from which the system processes the positional bias of the joint, the tremor amplitude and angular severity of the joint composition, such as flexion-extension, ulnar-radial, pronation-supination, and abduction-adduction. Depending on the type of signal being processed, RMS or power spectrum may be done for each of the degrees of freedom to process severity and composition data. The signals collected at each joint may be individually processed for each unique limb position during patient assessment.

Treatment regimens for movement disorders may encompass any useful treatments for the disorders of interest. Preferably, the treatment regimen comprises focal muscle treatment since one of the strengths of the present system and method is accurate determination of the particular muscles involved in the movement disorder. The treatment regimen may be, for example, injectable or non-injectable. Injectable treatment regimens involve injecting a drug or mixture of drugs (e.g. botulinum toxin (e.g. BoNT A, BoNT B, BTX-A, BTX-B), xylocaine, marcaine, or a nerve or muscle blocking agent) into one or more of the muscles involved in the abnormal movement. Non-injectable treatments include, for example, electromagnetic (e/m) radiation therapy, electromyogram stimulator, functional electrical stimulation, active orthotic device, ultrasound therapy, acupuncture, trans-cranial magnetic stimulation, topical application of drugs and the like. Combinations of treatments may be employed, for example drug injection together with muscle stimulation therapy.

One of the advantages of accurately determining the muscles involved in and their relative contributions to the abnormal movement is the ability to accurately determine the concentration and dose of a drug that each muscle requires to have injected therein. Thus, the drug may be administered to each muscle at a dosage based on the muscle group composition, the directional bias within each muscle group implicated in the abnormal movement and/or on the amplitude of the abnormal movement. In particular, the drug may be administered to each muscle at a dosage selected based on the amplitude of the abnormal movement. Amplitude may be measured in degrees as an angular deviation from 0. People without the abnormal movement typically show muscle movement amplitudes on the order of 0.03 to 0.07 degrees. Whether or not a specific deviation is sufficient to warrant administration of the drug to a muscle depends to some extent on the joint in question. For example, an abnormal movement having an amplitude at the wrist of less than about 0.3 degrees is not treated. For the elbow and shoulder, an abnormal movement having an amplitude of less than about 0.15 degrees is not treated. Also, the concentration of the drug may be especially determined by the size of the muscle group being treated. Muscles that have a greater contribution to the abnormal movement may be targeted with more of the drug than those with less contribution.

The dosage of drug injected into each muscle may be determined by following a procedure whereby amplitude of an abnormal movement at each joint guides the maximum dose of the drug to be injected into the muscles involved with joint, the muscle composition of the abnormal movement guides how the maximum dosage is divided between muscle groups, and the directional bias within each muscle group guides how the dosage given to a muscle group is divided between individual muscles. The procedure may be followed manually by a clinician, or the procedure may be embodied in a computer program or software and the dosages for each individual muscle determined from calculations based on sensor data and pre-set or inputted parameters. For example, total dosage for a joint may be correlated to amplitude data for the abnormal movement at the joint, whereby the amplitude may be compared to a standard curve of amplitude vs. total dosage or to a standard dosage for a range of amplitudes. More severe abnormal movements would warrant a greater total dosage. Once the total dosage for a joint is determined, composition data showing the relative contribution of each muscle group (e.g. abductors/adductors, flexors/extensors, etc.) may permit dividing the total dosage for that joint between the various muscle groups on a pro-rated basis, for example if abductor muscles were found to contribute 40% to the abnormal movement at the joint then abductor muscles would receive 40% of the total dosage of drug for that joint. Once the division of total dose between muscle groups has been determined, the dosage for each individual muscle in the muscle group can be determined from the directional bias on a pro-rated basis, for example within the abductor/adductor muscle group if abductors are responsible for 80% of the abnormal movement caused by the abductor/adductor muscle group then the abductor muscles would receive 80% of the dosage and the adductor muscles would receive 20%. Where one muscle falls within two or more muscle groups, that muscle would receive an amount of drug related to the sum of the dosages calculated for the muscle's contribution to the abnormal movement for each muscle group. In some cases, one muscle may be a contributor to abnormal movement at different joints, in which case the dosage received by that muscle would also be related to the sum of the dosages calculated for the muscle's contribution to the abnormal movement for each joint. Automation of the calculations in a computer program or software based on sensor data for amplitude, composition and directional bias and on standard total dosage correlations to the amplitude could standardize treatment decisions, improve the accuracy of treatment decisions and permit non-expert clinicians to make treatment recommendations.

Dosages of drugs will depend to a certain extent on the particular drug being used. For example, a dose range of: 10 U-60 U, especially 20 U-40 U or 10 U-30 U, of BoNT A can be used for each shoulder tremor contributing muscle; 10 U-50 U, especially 20 U-40 U or 10 U-30 U, of BoNT A for every elbow tremor contributing muscle; and 5 U-25 U, especially 5 U-15 U, of BoNT A for every wrist tremor contributing muscle (e.g. forearm and wrist muscles). All dosages are adjusted based on amplitude of the tremor. Likewise, if the composition and directional bias in one patient shows that the tremor is predominantly flexor at the wrist, a physician can optimize dosage based on medical experience to inject a higher dose in the flexor carpi radialis and flexor carpi ulnaris, and give lower doses to the extensor carpi radialis and extensor carpi ulnaris muscles. By Further, the present invention makes it possible to avoid injecting drugs into muscles that have no contribution to the abnormal movement. This reduces side effects and the amount of drug that is needed to be effective at treating the movement disorder.

In addition, and very importantly, the concentration of the drug may be increased, for example doubled, to reduce the occurrence of volume-dependent weakness in the muscles injected and also in the adjacent muscles due to the spread of the toxin. Thus, the same dose may be delivered in a smaller volume, for example half the volume.

Treatment regimens may be optimized and/or rehabilitation therapies implemented by iterating the methods of the present invention. A treatment regimen may be optimized after a first application of a therapy by analyzing the deconstructed kinematic sensor data for joints of the subject obtained for the first application of the therapy and the muscles and therapy parameters (e.g. drug dosages) selected for the first application in light of the outcome of the subject after the first application of the therapy. The results of such analysis may be used to determine adjustments to be made to location and extent (e.g. drug dosage) of the therapy in a second application of the therapy. This process may be repeated until an optimized regimen is obtained.

In one embodiment of an optimization process, a subject initially visits a clinician with a view to reducing the effects of the abnormal movement for reasons both cosmetic and functional. The clinician would assess the subject on the usual clinical scales and classify the subject based on the type of abnormal movement. The subject's strength in the affected limbs is measured and then the subject is subjected to kinematic assessment as described herein. As a first step in the kinematic assessment, the subject is fitted with kinematic sensors and the sensors calibrated. During calibration and subsequent data collection, it may be important to position the subject's limbs in such a way as to eliminate bias due to gravity. Sensor data may then be collected on all of the abnormal movements of the subject, and the sensor data processed to determine severity (amplitude), angle and bias of each abnormal movement. The amplitude, angle and bias may then be deconstructed into muscle composition and directional bias, which yields the particular muscles involved in and their respective contributions to each abnormal movement. Based on the muscles involved and their relative contributions, a treatment regime may be determined by a physician that indicates where the subject would be treated (i.e. which muscles) and the extent of therapy (e.g. the dosage of drug at each muscle).

In a follow-up visit to the clinician, for example 1-10 weeks after the initial treatment (e.g. 6 weeks), the subject is once again clinically assessed and strength measurements taken. Kinematic assessment is again performed and the sensor data eventually deconstructed to muscle group composition and directional bias. Based on the clinical and kinematic assessments compared to the assessments performed in the first visit, the clinician determines what, if any, improvement has occurred and whether any optimization to the treatment regimen is possible. If the subject has developed a weakness in one or more muscles as a result of the first treatment regime (e.g. the first administration of a drug), the regimen may be optimized by reducing the extent of therapy (e.g. reducing dosage of the drug) to the one or more muscles that developed the weakness. If there is an insufficient reduction in the amplitude of the movements caused by the movement disorder at a given joint and a change of 10% or more in the muscle composition of the movements caused by the movement disorder at the given joint, the regimen may be optimized by increasing the extent of therapy (e.g. increasing dosage of a drug) to the muscle group that has become the most dominant contributor to the movement caused by the movement disorder at the given joint, provided that the muscle group receiving the increased therapy does not comprise one or more muscles that developed a weakness. The treatment regimen may be further optimized by asking the subject whether the movement disorder has improved, and if the subject reports that the movement disorder has not improved then increasing the extent of therapy (e.g. dosage of the drug) may be undertaken at each muscle that previously received the therapy without providing therapy to muscles that did not previously receive therapy, provided that the therapy is not increased in any muscle that developed a weakness or any muscle that is receiving an increased in therapy due to other optimization decisions.

In a third visit, for example 11-20 weeks (e.g. 16 weeks) after the initial visit, the clinical assessment including strength measurements is repeated and the information generated from all three visits is used to determine whether no dose, the same dose, a higher dose or a lower dose of the therapy is required, as well as any changes to muscle groups selected should be implemented.

In a rehabilitation therapy, a time course of treatment may be prescribed based on kinematic assessment and recurrence of the abnormal movements after initial treatment. Initial treatments may result in a decrement in the magnitude and/or frequency of the abnormal motions observed, and repeated application of the therapy guided by kinematic assessment may reduce the magnitude of the motions and/or increase the amount of time required between therapy events. This leads to long term suppression of the disorder. Further, movement disorders may also comprise a neurological component in which the brain has been conditioned over time to trigger the abnormal movements associated with the movement disorder. Treatment of the muscle involved to reduce the severity of the abnormal movements may help re-condition the brain providing a feedback loop to reduce abnormal movement without the aid of therapy. Therefore, accurate muscle selection and treatment parameters (e.g. dosing) would help re-condition the brain providing a long-term solution to the movement disorder. Only optimal treatment regimens would be useful in this regard, so developing treatment regimens based on kinematic assessment as disclosed herein would be greatly preferred over the currently employed visual assessment strategies. In some treatment regimes, treating only one side of a subject's body may lead to benefits for the other side of the body.

Subtle motions and the muscles involved in movement disorders are generally too difficult for clinicians to visually assess. Visual assessment is therefore a subjective and clinician-experience dependent assessment tool. Although all movement disorder may be visually diagnosed, current visual assessment is generally limited because: human eyes are not at a level needed to properly pin-point the location of symptoms; movement disorders change from task to task, which his not traceable by human eyes; and, movement disorders change over time, which is not traceable and comparable through notes and visual assessment. The present system and methods are able to provide a breakdown of motions that is accurate and objective. Such accuracy leads to more appropriate treatment at the correct muscles involved in the movement disorder, which leads to greater efficacy of treatment, reduction in the amount of therapy required and fewer side effects. For example, use of the present system and methods in conjunction with BoNT A injection therapy increases the effectiveness of BoNT A, reduces the dose required, increases functionality of treated limbs and reduces muscle weakness, muscle weakness having been a side effect of BoNT A therapy. Further, objective sensor data analyzed in a consistent way permits accurate tracking of the progression of the movement disorder following medical intervention.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

In FIG. 4A for PD subject #6 at rest, the tremor was predominantly P/S with minimal F/E or R/U deviations. In FIG. 4B for PD subject #2 in posture, the tremor was a combination of F/E and P/S. In FIG. 4C for ET subject #10 in posture, the tremor was predominantly F/E with slight P/S.

FIG. 5A, depicts the placement of torsiometer, goniometer and accelerometric sensors for the shoulder (goniometer), elbow (goniometer), wrist (goniometer), dorsal surface of hand (accelerometer) and front of forearm (torsiometer). FIG. 5B, shows the placements of IMUs sensors on the whole arm. FIG. 5C, demonstrates the positioning of markers needed for the capture of tremor movements using camera and IR tracking devices. FIG. 5D shows the placement of magnetometric sensors in order to record tremor in the arms.

FIG. 8A shows the placement of torsiometer on the neck and inclinometers on the head and shoulders. FIG. 8B shows the placement of IMUs for measuring neck tremor and dystonia. FIG. 8C shows the location of markers needed to accurately utilize camera and IR based tracking devices. FIG. 8D shows the location of magnetometers on the head and shoulder needed for measuring cervical dystonia.

FIG. 11A depicts data for tremor angle, severity, composition and bias at joints in a left arm of an Essential Tremor (ET) subject.

FIGS. 11B-J depict a process for determining the dosage of BoNT A to be injected into each muscle of the left arm of the ET subject based on the data in FIG. 11A.

DESCRIPTION OF PREFERRED EMBODIMENTS

EXAMPLES

Figure 1:
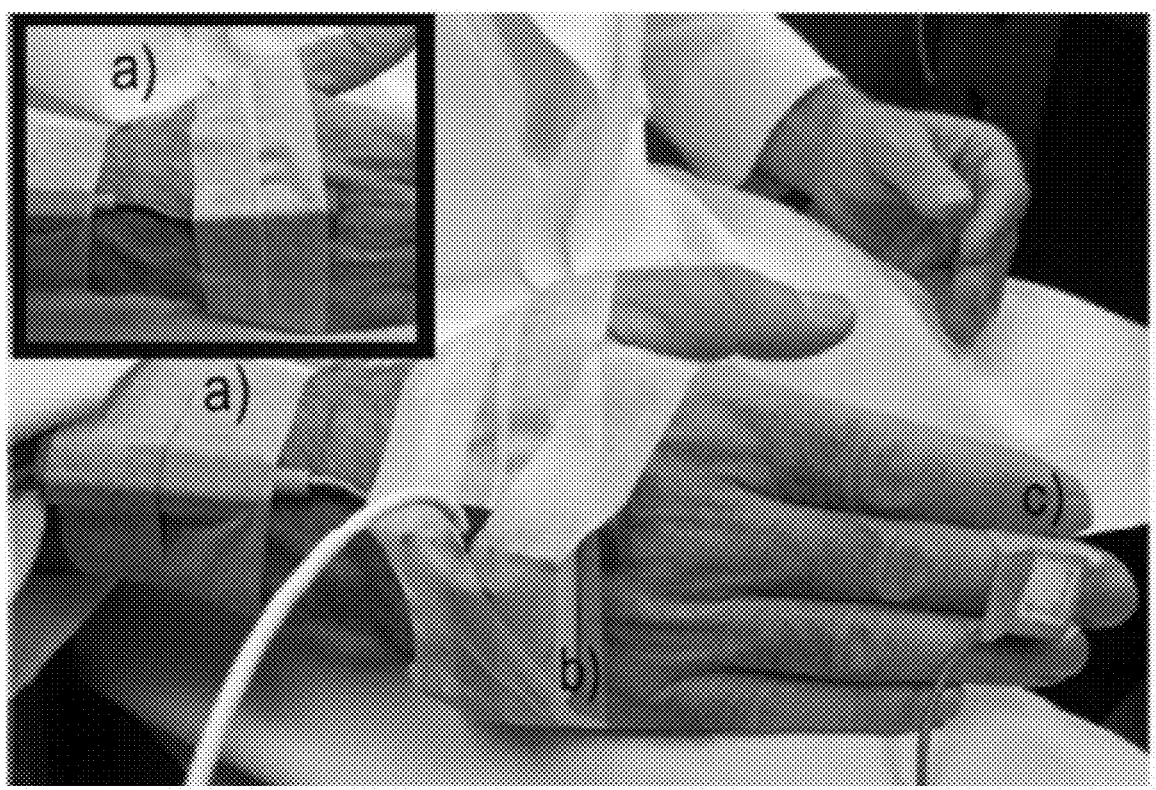
FIG. 1 depicts placement of kinematic sensors on forearm, hand and wrist of a subject for measuring joint movement during tremor. Tremor was measured by angle at the wrist, and by acceleration at the interphalangeal joint, where a) is an electro-goniometer measuring wrist F/E and R/U, b) is an inclinometer measuring forearm P/S, and c) is a light-weight 3D accelerometer collecting distal finger movements as a measure of overall tremor severity.

Example 1: Kinematic Assessment of Tremor Composition and Directional Bias in a Wrist Kinematic methodology is well established for studying the dynamics of movement in the upper limb. Technological advances have made this a reliable and viable option in the characterization of complex movements such as tremor. Wrist tremor, for example, is variable and has three directions of movement: flexion/extension (F/E), radial/ulnar (R/U), pronation/supination (P/S). Hence, visually-guided judgment of the complexity of movement over time may be difficult and inaccurate. Further, kinematic studies to date have not deconstructed the complex movements into their muscle compositions and directional biases within muscle groups. As described herein, kinematic methodology can accurately allow for assessment of all these variables, leading to improved characterization of tremor dynamics. In order to understand the biomechanics of tremor in both ET and PD, the composition of these tremor types in a wrist was evaluated kinematically, the complexity of dynamics of the tremor demonstrated, and the kinematic evaluation compared to traditional visual evaluation of tremor composition.

A convenience sample of ET and PD patients was recruited for participation in the study by a single Movement Disorders Neurologist from a tertiary care movement disorders clinic. Patients were enrolled in a larger ongoing study on the optimization of BoNT A injection for focal hand tremor over an 8 month period. Baseline data for the first 11 patients with clinically confirmed ET and 17 with PD were studied (Table 1). The diagnosis of ET by a movement disorders specialist was based on the current standards [Benito-Leon 2011; Deuschl 1998]. All PD patients met the UK Brain Bank criteria for PD. Inclusion criteria involved all subjects to be on stable medication management a minimum of 6 months prior to enrolment with none withheld for this study, to have tremor as their primary and most bothersome symptom, and to be botulinum toxin naive. None of the subjects had other neurological disorders. For data recording, the motor dominant hand was considered for the ET patients. In PD patients, the hand reported to have the larger tremor amplitude was assessed, regardless of handedness, and all kinematic assessments were carried out in the "on" medication state.

TABLE 1

Subject Demography for ET and PD

| | ET | | | | | PD | | | |
|---|---|---|---|---|---|---|---|---|---|
| ID | Age | Gen | Yrs | Side | ID | Age | Gen | Yrs | Side |
| 1 | 64 | M | 10 | R | 1 | 47 | M | 11 | R |
| 2 | 70 | F | 33 | R | 2 | 66 | M | 3 | R |
| 3 | 74 | F | 11 | L | 3 | 55 | M | 1 | R |
| 4 | 69 | M | 4 | R | 4 | 57 | F | 6 | L |
| 5 | 75 | M | 60 | R | 5 | 71 | M | 5 | R |
| 6 | 72 | M | 6 | R | 6 | 58 | M | 7 | R |
| 7 | 66 | M | 7 | R | 7 | 60 | F | 6 | R |
| 8 | 74 | M | 4 | R | 8 | 69 | M | 25 | L |
| 9 | 75 | F | 50 | R | 9 | 67 | F | 5 | L |
| 10 | 80 | F | 3 | R | 10 | 63 | M | 6 | R |
| 11 | 47 | M | 20 | L | 11 | 62 | M | 4 | R |
| | | | | | 12 | 80 | M | 1 | R |
| | | | | | 13 | 74 | M | 9 | L |
| | | | | | 14 | 72 | M | 7 | L |
| | | | | | 15 | 60 | M | 4 | R |
| | | | | | 16 | 67 | M | 6 | L |
| | | | | | 17 | 67 | F | 5 | L |
| Avg | 69.6 | | 18.9 | | | 64.4 | | 6.5 | |
| SD | 8.8 | | 20.0 | | | 8.0 | | 5.4 | |

ID = participant's identification number
Gen = gender
Yrs = years with tremor
Avg = average
SD = standard deviation Kinematic Methods Kinematic devices were used to record composition of wrist tremor, in addition to overall tremor amplitude/severity. Wrist flexion/extension (F/E) and radial/ulnar deviation (R/U) were measured using a twin flexible axis electro-goniometer (SG65, Biometrics Ltd) placed across the wrist joint. Forearm pronation/supination (P/S) was measured using a 2D inclinometer (Noraxon®) secured to the dorsal surface of the hand. Together, the sensors provided 3 degrees of freedom (DOF) angular measurements at the wrist. Finger tremor was also recorded using a linear accelerometer (3D, 6 g, Noraxon®) at the distal interphalangeal joint of the middle finger giving three degrees of linear acceleration. FIG. 1 illustrates placement of the sensors.

This measure provided an overall measure of tremor severity. While the electro-goniometer recorded relative motion of the wrist and the forearm, the inclinometer and the accelerometer had a global inertial frame of reference. The sensors were attached to standard positions using medical grade tape, and were connected to a laptop through TeleMyo 2400T G2 and PC interface. Data were digitally sampled (at 1500 Hz, using MyoResearch XP Master Edition 1.08.09 software, Noraxon®) and saved for off-line processing and analysis.

All recordings were performed in the seated position. After attaching the sensors, the hand was placed against a fixed vertical plane in neutral P/S, neutral R/U deviation, and neutral F/E for the wrist and elbow. Five seconds of data in this neutral position at this neutral position was used for calibration. Subjects then performed a series of 3 tasks: rest, posture, and posture-neutral (posture-neut), each 10 seconds in duration and ask to not resist or correct for their tremor movement. During rest position, subjects placed their relaxed hands in neutral pronation on their lap. Posture position had subjects extend both arms outwards in front parallel to the ground with their hands out and palms facing the floor. Posture-neutral was the same position with the exception to hand orientation, by having the palms face each other. These series of tasks were repeated a total of 3 times. Only the 2 tasks of rest and posture that are classically assessed in clinical neurological exam to elucidate tremor were used in composition analysis. Directional bias was studied in the pronated position for R/U and in posture-neut position for F/E and P/S. These limb positions were selected to avoid confounding effect of gravity.

Signal processing was performed in MatLab® (MathWorks, R2011a). For each subject data file, the segments corresponding to each trial were extracted for every task. Each segment included three angular position signals for the wrist, and three linear acceleration signals for the finger. For each angular position signal, the mean value during neutral position calibration was subtracted before further processing. All tremor signals (both angular position and acceleration) were band-pass filtered (2-20 Hz, least-squared finite impulse response filter, order 2000). Signals were symmetrically padded on both ends. For each tremor signal, after filtering, root-mean-squared (RMS) value was calculated as the measure of amplitude to avoid filter transient effects. Amplitude for 3D finger tremor, amplitude for 3-components of wrist tremor, and directional bias of each component during trials were calculated for 3-trials of rest and for 3-trials of posture. Three dimensions of linear acceleration at the finger were combined (RMS) to provide overall tremor severity. Percent contribution for each of the three components to wrist tremor was determined with respect to the summed 3D angular amplitude (F/E+R/U+P/S). Directional bias for each of the 3-components were calculated by averaging the signal, taking into account direction (positive=F/R/P; negative=E/U/S).

Tremor acceleration amplitudes usually have skewed distributions and log-transformation. Therefore, overall finger tremor (combined 3D) amplitudes were log-transformed before analysis. The log-transformed data met criteria for parametric analysis. Average amplitude over three trials was compared in a 2-way ANOVA between effects of diagnosis and repeated measures for rest and postural positions. Alpha level was set at 0.05 and Tukey's HSD test was conducted for post-hoc analysis.

Percent contribution for each of the three components of wrist tremor was averaged over 3 trials.

The averaged directional bias data over three trials met criteria for parametric analysis. For each group of subjects, a separate univariate ANOVA compared directional bias in each of the wrist tremor components (F/E, R/U, P/S). Confidence intervals (95%) were used to examine if the average bias for a component was significantly positive or negative. Statistical analyses were performed in STATISTICA® 8.0, StetSoft Inc.

Visual Methods

To compare kinematic assessment to the prior art standard visual assessment, the following clinical scales of visual tremor assessment were available for 8 ET and 11 PD patients. A single assessor conducted the administration of Unified Parkinson's Disease Rating Scale (UPDRS) for the hand to be injected. Items 20 (rest tremor: hands L/R) and 21 from UPDRS (hands action tremor: L/R) are specific visual assessments relating to tremor and upper limb and were collected for all patients. In the same data collection session, subjects were asked to draw the Archimedes spiral and a straight line as part of Fahn-Tolosa-Marin tremor rating scale for both hands [Fahn 2003]. Tremor scores in lines and spirals drawing ranged from 0-4, and were evaluated by a separate assessor for all patients.

Comparison Between Kinematic and Clinical Derived Schemes

For the same group of subjects with recorded clinical scales (8 ET and 11 PD patients), effect of tremor evaluation method on the choice of muscles selected for potential injection was examined. The clinical assessment was based on visual observation and the scores of the clinical scales used as described above. The clinician selected the muscle groups for injection and the dosages that may be required for BoNT A injections (called Scheme 1).

After recruitment of all subjects, kinematic analysis data was presented in a randomized order to the same clinician who was blinded to the clinical assessment of the patients. Kinematic data gave the direction of the movement, the amplitude and the relative contributions of each tremor component without any identifiers (see FIG. 2). These pairs included P/S at the forearm, F/E and R/U at the wrist.

Similar to the visually-based clinical determination, the clinician then selected injection parameters including the muscles and the possible dosage of BoNT A for optimized outcome (called Scheme 2).

Results

Eleven ET patients (70±8.8 years) and 17 PD patients (64±8.0 years) were assessed with the demographics summarized in Table 1 above. The summary of tremor scores is presented in Table 2. Average finger tremor (acceleration, before log transformation) and wrist tremor (angle) amplitudes over all rest and posture trials are also presented for each subject. Summed Items 20 (only hand) and 21 from UPDRS are presented for each subject along with the scores in line and spiral drawings.

Since the 3D accelerometric measurement at the finger would show tremor originating from the fingers, wrist and elbow, the finger tremor amplitude was used to represent overall tremor severity. Tremor amplitude of ET at rest was significantly lower ($F(1, 26)=5.25$, $p=0.030$, and post-hoc Tukey's HSD test) than ET at posture, while PD at rest and posture were not significantly different. In addition, ET and PD at posture were also not significantly different. These data are presented in FIG. 3A.

In order to compare overall tremor severity between kinematic and clinical measures (UPDRS tremor score), acceleration amplitudes at rest and posture for finger tremor were averaged over 3 trials. Wrist angle was also averaged in the same way. These two measures were then individually compared to the summed Items 20 and 21 of the UPDRS, which served as a clinical indicator of overall tremor. Since the finger movement was recorded as an acceleration and wrist movement as an angle, these could not be summed. There was a strong linear dependence between UPDRS Items (20+21) and the kinematic measures of tremor amplitude in both ET and PD (Pearson's correlation coefficient, $r=0.84$, $r=0.84$ for log-transformed average finger tremor, and for average angular wrist tremor amplitudes respectively).

TABLE 2

Clinical and Kinematic Tremor Scores

| ID | F-R | F-P | W-R | W-P | I-20 | I-21 | Sprl | Line |
|---|---|---|---|---|---|---|---|---|
| ET | | | | | | | | |
| 1 | 1.08 | 0.55 | 0.42 | 0.25 | 2 | 2 | 2 | 2 |
| 2 | 0.14 | 0.29 | 0.05 | 0.24 | 0 | 3 | 3 | 3 |
| 3 | 0.37 | 3.13 | 0.30 | 2.51 | 2 | 3 | 4 | 4 |
| 4 | 0.12 | 0.67 | 0.09 | 0.87 | 0 | 2.5 | 2 | 2 |
| 5 | 0.08 | 0.09 | 0.04 | 0.06 | 1 | 2.5 | 4 | 4 |
| 6 | 0.01 | 0.11 | 0.15 | 0.71 | 0 | 3 | 2 | 2 |
| 7 | 0.14 | 0.62 | 0.69 | 2.31 | 0 | 3 | 1 | 1 |
| 8 | 0.02 | 0.02 | 0.16 | 0.17 | 0 | 2 | 2 | 1 |
| 9 | 0.09 | 0.16 | 0.08 | 0.13 | | | | |
| 10 | 0.05 | 0.17 | 0.06 | 0.19 | | | | |
| 11 | 0.11 | 0.30 | 0.19 | 0.29 | | | | |
| Total | 0.2 ± 0.3 | 0.6 ± 0.9 | 0.2 ± 0.2 | 0.7 ± 0.9 | 0.6 ± 0.9 | 2.6 ± 0.4 | 2.5 ± 1.1 | 2.4 ± 1.2 |
| PD | | | | | | | | |
| 1 | 4.99 | 6.97 | 2.09 | 6.19 | 3.5 | 3 | 3 | 2 |
| 2 | 1.02 | 3.17 | 0.28 | 0.62 | 2.5 | 2.5 | 0 | 0 |
| 3 | 0.08 | 0.14 | 0.04 | 0.10 | 3 | 0 | 0 | 0 |
| 4 | 3.91 | 5.21 | 1.35 | 2.79 | 3 | 2.5 | 4 | 4 |
| 5 | 0.40 | 0.34 | 0.24 | 0.15 | 2 | 1 | 1 | 1 |
| 6 | 4.03 | 5.59 | 2.51 | 2.47 | 3.5 | 3 | 1 | 0 |
| 7 | 0.11 | 0.30 | 0.07 | 0.15 | 3 | 1 | 1 | 1 |
| 8 | 2.53 | 5.76 | 0.49 | 1.40 | 2.5 | 2 | 4 | 4 |
| 9 | 0.33 | 0.26 | 0.30 | 0.18 | 1.5 | 1 | 1 | 1 |
| 10 | 0.28 | 0.23 | 0.20 | 0.19 | 2 | 0 | 0 | 0 |
| 11 | 0.06 | 0.10 | 1.98 | 0.08 | 3 | 0 | 1 | 0 |
| 12 | 0.19 | 0.23 | 0.14 | 0.12 | | | | |
| 13 | 0.08 | 0.15 | 0.05 | 0.08 | | | | |

TABLE 2-continued

Clinical and Kinematic Tremor Scores

| ID | F-R | F-P | W-R | W-P | I-20 | I-21 | Sprl | Line |
|---|---|---|---|---|---|---|---|---|
| 14 | 0.37 | 0.22 | 0.32 | 0.12 | | | | |
| 15 | 1.11 | 1.95 | 0.74 | 0.74 | | | | |
| 16 | 0.21 | 0.73 | 0.10 | 0.35 | | | | |
| 17 | 6.61 | 7.01 | 4.30 | 4.82 | | | | |
| Total | 1.5 ± 2.1 | 2.3 ± 2.7 | 0.9 ± 1.2 | 1.2 ± 1.8 | 2.7 ± 0.6 | 1.5 ± 1.2 | 1.5 ± 1.5 | 1.2 ± 1.5 |

ID = participant's identification number
F-R = finger acceleration tremor (g) at rest
F-P = finger acceleration tremor (g) in posture
W-R = wrist angular tremor (degree) at rest
W-P = wrist angular tremor (degree) in posture
I-20 = UPDRS item 20 score (only hand)
I-21 = UPDRS item 21 score
Sprl = spiral drawing score
Line = line drawing Score
Avg = average
SD = standard deviation There was no significant difference in summed UPDRS scores of hand rest and postural tremors between ET patients (95% CI [2.6, 3.9]) and PD (95% CI [3.2, 5.0]) implying that there was no difference in the two groups for tremor severity. However, separated UPDRS Item 20 (hand tremor at rest: ET: [0, 1.3], PD: [2.3, 3.1]) and 21 (action tremor: ET: [2.3, 2.9], PD: [0.7, 2.2]) were significantly different between the two groups of patients. Similarly, the kinematic measures at rest and posture in ET and PD showed no significant difference (finger rest: ET: [0.0, 0.5], PD: [0.5, 2.7]; finger posture: ET: [0.0, 1.4], PD: [0.9, 4.2]; wrist rest: ET: [0.1, 0.4], PD: [0.3, 1.4]; wrist posture: ET: [0.2, 1.6], PD: [0.2, 2.4]). No significant differences were found in line drawing (ET: [1.8, 3.2], PD: [0.6, 2.3]) or spiral drawing (ET: [1.6, 3.1], PD: [0.3, 2.0]) scores.

The composition of tremor, for both groups of subjects and for both tasks of rest and posture, is presented in FIG. 3B and FIG. 3C. For ET at rest, none of the components was found to dominate the wrist tremor (Kruskal-Wallis test: H(2, N=33)=3.76, p=0.153). For ET in posture, F/E was found to dominate the other two components (H=12.26, p=0.002). For PD both at rest and in posture, F/E was significantly larger than R/U (H(2, N=51)=6.28, p=0.043; H=12.78, p=0.002 respectively), but not from P/S.

In order to divide each degree of freedom separately, we calculated the directional bias for each pair of antagonist muscles at the wrist (F vs. E, R vs. U, P vs. S) and not at the finger. This indicated whether one directional component dominated for both ET and PD. The average directional bias for each of the 3 wrist tremor components and for both groups of subjects is presented in FIG. 3D and FIG. 3E. For both groups of subjects, directional bias was significantly different among the components (ET, F(2, 30)=4.84, p=0.015; PD, F(2, 48)=36.18, p<0.001). For ET patients, the only significant average bias was for P/S which was toward pronation. For PD patients, all three components had significant average directional biases. The bias for F/E was toward extension, for R/U toward ulnar deviation, and for P/S toward pronation. With respect to composition, wrist tremor movements were often complex with none of the components (F/E, R/U and P/S) clearly dominating the tremulous motion. To assess this complexity, a component was deemed to be dominant if contribution was >70% (arbitrarily). For each subject, rest and posture trials were separately averaged for ET and PD, and then evaluated for the occurrence of any component above this threshold. This analysis revealed that for ET the dominance percentages were (rest: 0%, posture: 36%) and for PD (rest: 23%, posture: 23%). As an example, wrist tremor composition for three different subjects is demonstrated in FIG. 4 showing that for each subject, the tremor composition was unique to that subject.

This Example demonstrates that tremor, in both rest and posture, is present in ET and PD. In ET, the tremor is clearly posture predominant while in PD both rest and posture were equal in the cohort. The amplitude of PD tremor was overall higher in the subjects. In addition, significant variability existed in the tremor amplitude. These results are shown in panels A of FIG. 2 and FIG. 3. The postural component of PD tremor in the cohort may be a result of patients with more severe tremor than a typical PD patient, but it emphasizes the point that tremor in posture can exist with as much severity in PD as rest and may contribute to functional disability doing tasks.

Figure 3:
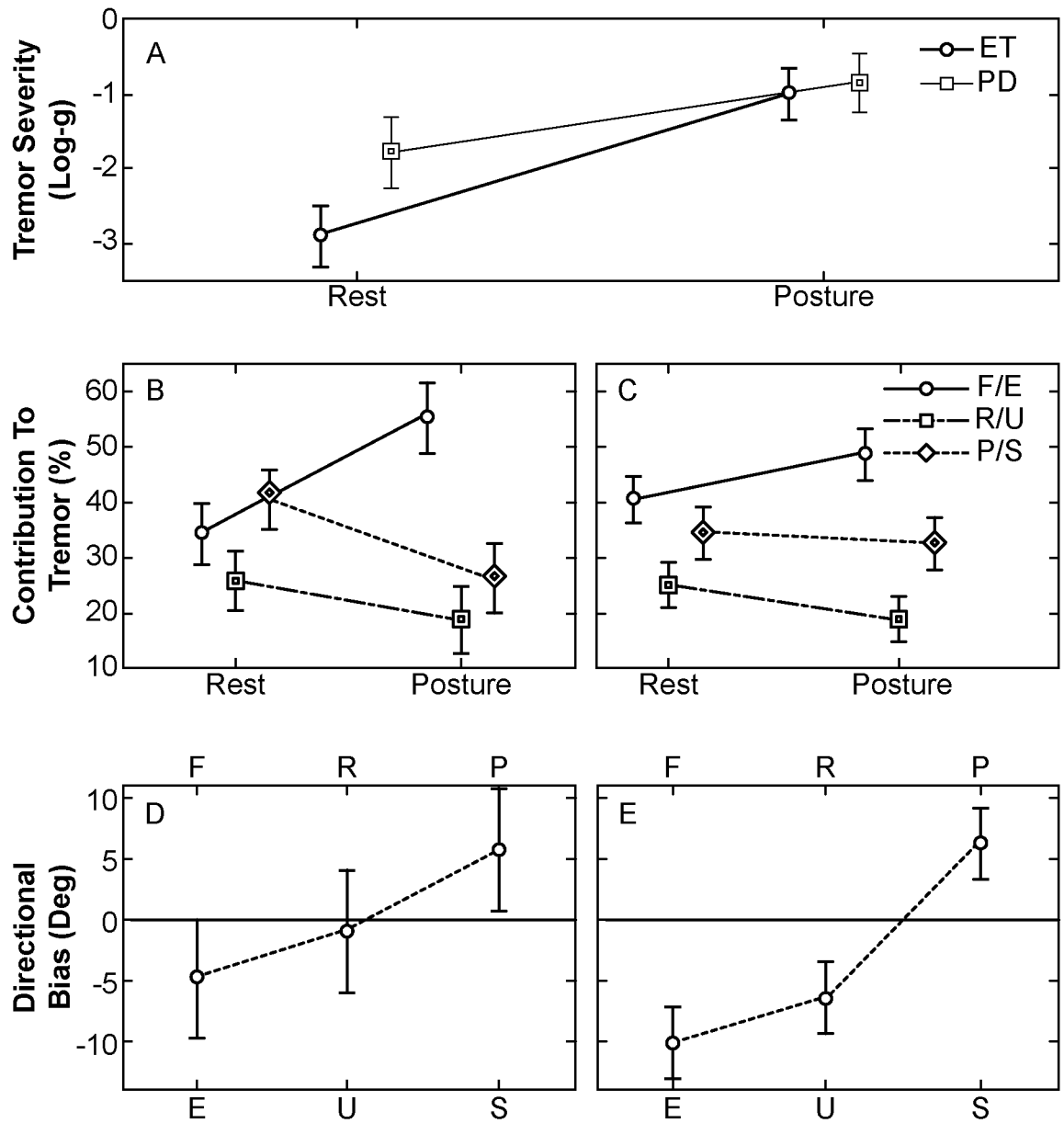
FIG. 3A depicts a graph showing finger amplitude for overall tremor severity for ET and PD averaged over 3 trials of each condition.
FIG. 3B depicts a graph showing composition of wrist tremor contrasted between rest and posture tasks for ET.
FIG. 3C depicts a graph showing composition of wrist tremor contrasted between rest and posture tasks for PD.
FIG. 3D depicts a graph showing directional bias across 3-DOF in wrist tremor for ET.
FIG. 3E depicts a graph showing directional bias across 3-DOF in wrist tremor for PD. Contribution was calculated for each DOF (F/E, R/U, and P/S) amplitude with respect to the sum of all 3-DOF amplitudes. Confidence interval outside zero (neutral) was considered significant bias.
Figure 4:
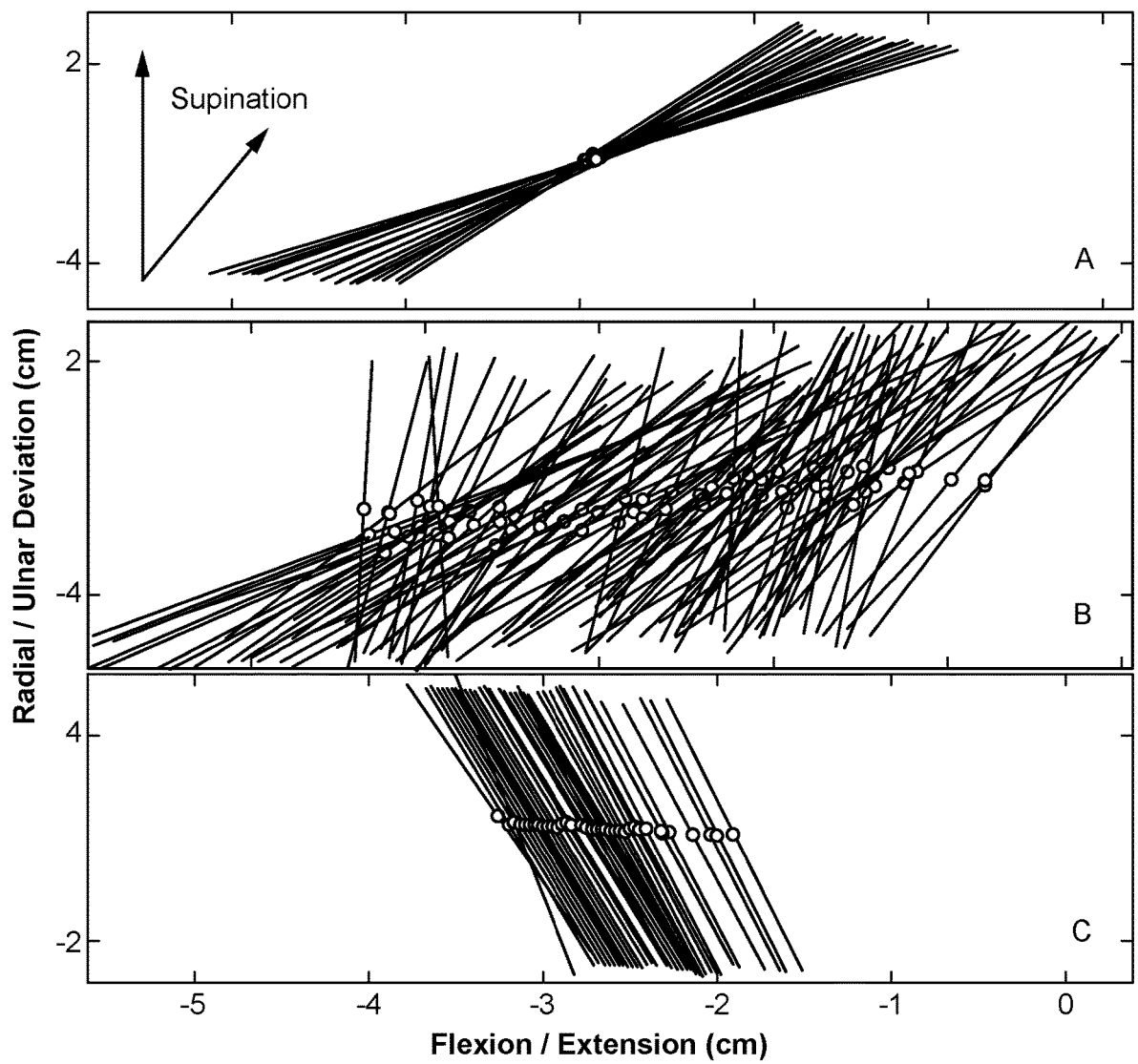
FIG. 4 depicts a graph illustrating wrist tremor complexity in 3 DOF for 3 subjects. Each line represents the motion of the wrist recorded every 0.1 sec. Movement of the dot along the X-axis represents F/E, along the Y-axis R/U, and the line rotation (angle) representing P/S.

The complex composition of tremor in ET and PD is clearly shown in panel B and C of FIG. 3, respectively. In ET, at rest, all three components of F/E, R/U and P/S are contributing almost equally. With posture, this composition changes significantly so that F/E becomes predominant. However, P/S and R/U do persist but at a much lower proportion. Hence, if a patient has predominant posture related issues with ET, the suggestion would be to begin injections with BoNT A with those muscle groups that contribute to flexion and extension. If the patient is also seen to have rest tremor and the diagnosis is still ET, then additional injections with P/S and R/U can be considered. Analysis of the directional bias of these components with respect to the contributions towards movement as seen in FIG. 3D show that the injections should be equally divided between the muscle groups contributing to F/E and R/U while pronators should receive more than supinators, because pronators were statistically biased from neutral. It should be noted that this is a global impression of contribution and personalized muscle injections are based on the subject's individual assessment and unique characteristics.

FIG. 3C also shows that in PD tremor F/E and P/S were equally significant at rest and in posture and contributed significantly higher than R/U in both conditions. This suggests that when considering injections for PD tremor, both of these movement subcomponents should be injected from the start and probably in equal amounts. Analysis of directional bias of these components with respect to the contribution towards the tremor for these patients shows that the injection amounts should be divided between the antagonist muscles such that extensors should receive more than flexors; ulnar deviators more than radial deviators, and pronators more than supinators. One can suggest a decision tree where, ECR and ECU are injected with ECU>ECR while PRQ and PRT are injected more than SUP and potentially Biceps. Injection dosages of BoNT A to be used for injection are generally known to the skilled physician. Based on kinematic analysis of tremors in an individual subject such as described herein, the skilled clinician can select the appropriate dosage levels for that subject.

Figure 2:
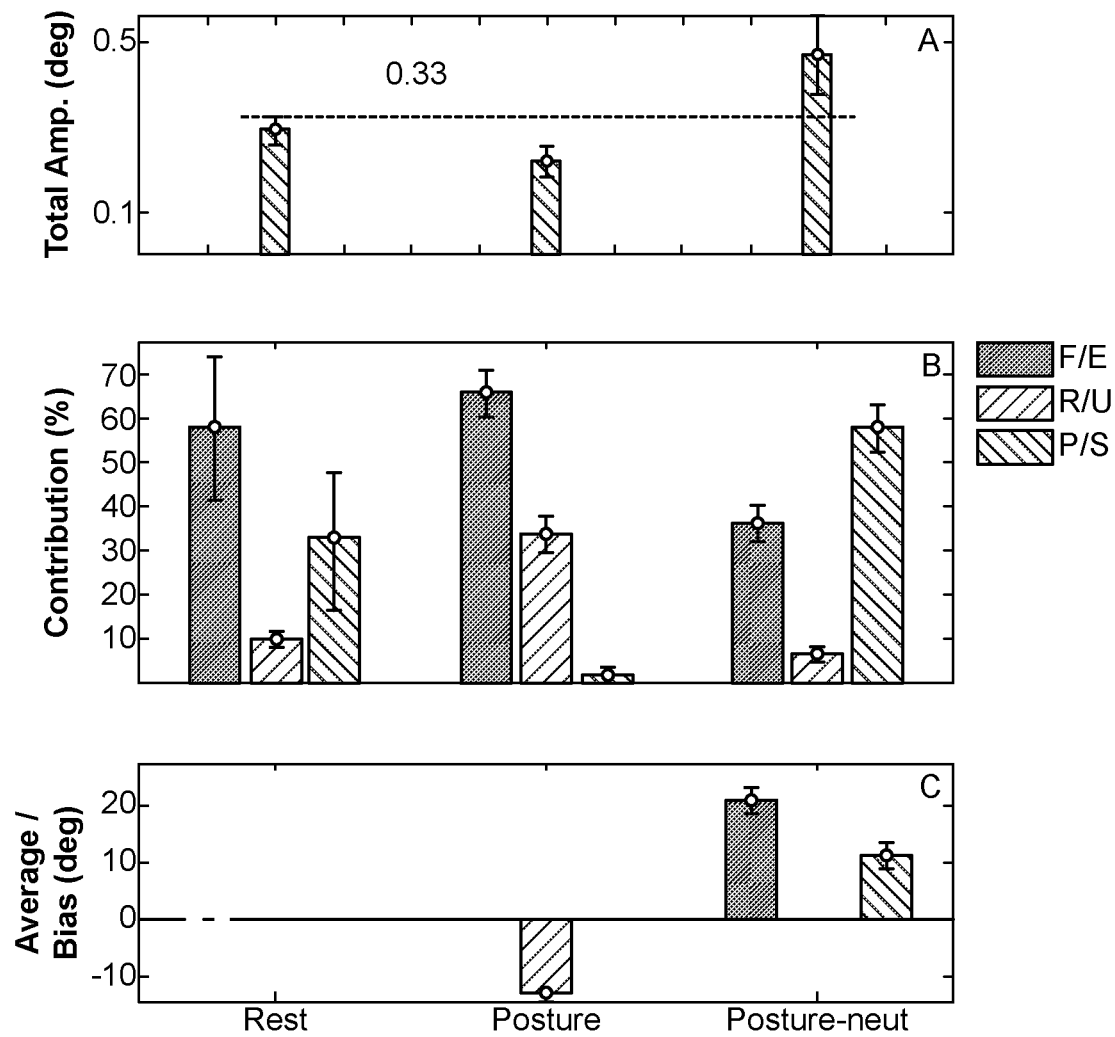
FIG. 2 depicts a graph showing amplitude, composition, and directional bias of tremor at the wrist for PD subject #9. The top row shows the RMS (root mean square) combined amplitude of the 3-DOF in wrist tremor. For rest, posture and neutral posture, mean and standard deviations of the amplitude for the three trials are presented. The grand average (horizontal line) is also presented. B) The contribution of each component (F/E, R/U, and P/S) to the wrist tremor for each posture. C) The directional bias in each group of antagonist muscles (DOF). For P/S and F/E such a situation would be posture in neutral pronation (posture-neut). The figure shows that this tremor was predominantly a F/E and P/S type tremor at rest with bias towards flexion and pronation.

This Example showed significant variability in the tremor parameters within (FIG. 2) and between (FIG. 3) subject groups. It has been already shown that, after tremor amplitude, the second most variable factor in wrist tremor is its composition. Furthermore, change in the task might considerably change the composition of wrist tremor (FIG. 2). This means that a single and simple visual inspection of tremor in one situation might not be enough. In a clinical setting it is extremely difficult to observe a subject's tremor in a variety of different positions and determine the overall composition of the tremor. Indeed, the clinician does not have the ability to summate over a period of time or over different positions. Due to this variability and the difficulty in perceiving this by simple visual inspection, it is quite likely that the muscle selection may not be optimal.

Thus, tremor deconstruction showed motion was dominated (>70% contribution) by 1-DOF in ET (rest: 0%, posture: 36%) and PD (rest: 23%, posture: 23%). Task variation in ET and PD resulted in change in amplitude and composition. Amplitude significantly increased from rest to posture in ET, but this increase was not significant in PD. Composition change was significant in ET only. Directional bias in each DOF was observed at the wrist joint for pronation in ET, and for extension, ulnar deviation, and pronation in PD.

Agreement between Scheme 1 (visual) and Scheme 2 (kinematic) in selecting muscles that contribute to tremor was then evaluated. When a specific muscle appeared in both the schemes, an agreement number of 1 was assigned, while if the muscle appeared in only one of the two schemes, the number was 0. The determination was done for every muscle that was used in the schemes and the list is presented, with the agreements in Table 3.

Since the determination of the predominant characteristics of motion in the tremor is done visually, the composition and the subsequent muscle for injection done by the visual method was compared to what was provided by the kinematic assessment. Low agreement between clinical assessment in the hands of an experienced injector and what was given by the objective kinematic assessment highlights the inherent difficulty of visual assessment of such complex tremor. Table 3 shows that overall there was only a 36% and 53% agreement for muscles chosen visually versus in the blinded kinematic assessment, for ET and PD respectively. Thus, the difference in muscle selection for potential injection made by visual clinical versus kinematic assessment of tremor dynamics in a blinded fashion by the same injector was highlighted.

TABLE 3

Agreement in All Muscles Selected for Injection

| Muscle Name | Abr. | ET Presence | ET Agree (%) | PD Presence | PD Agree (%) |
|---|---|---|---|---|---|
| Flexor carpi ulnaris | FCU | 8 | 50 | 11 | 64 |
| Flexor carpi radialis | FCR | 7 | 57 | 10 | 70 |
| Extensor carpi ulnaris | ECU | 7 | 29 | 8 | 75 |
| Extensor carpi radialis | ECR | 7 | 29 | 8 | 63 |
| Supinator | SUP | 6 | 33 | 8 | 50 |
| Pronator teres | PRT | 6 | 33 | 7 | 57 |
| Pronator quadratus | PRQ | 5 | 40 | 6 | 17 |
| Biceps brachii | BIC | 4 | 0 | 5 | 20 |
| Triceps brachii | TRI | 0 | 0 | 1 | 0 |
| Flexor digitorum superficialis | FDS | 0 | 0 | 1 | 0 |
| Flexor pollicis longus | FPL | 0 | 0 | 1 | 0 |
| Overall Agreement | | | 36% | | 53% |
| # Muscles Selected Kinematically | | 4 | | 4 | |
| # Muscles Selected Clinically | | 5 | | 5 | |

The first and second columns list all the muscles with abbreviations.
Presence = numbers of subjects where that particular muscle was chosen
Agree = the percentage agreement for that muscle between Scheme 1 and Scheme 2.

Kinematic analysis of tremor, such as outlined in this Example, to determine composition and directional bias of muscles involved in the tremor provides an objective, non-visual method of assessing where and how much drug to administer to a subject to control the tremor. This analysis highlights the limitation of visual assessment of the complexities of tremor in ET and PD.

Example 2: Treating Arm Limb Tremor and Deviation Using Kinematic Analysis and Botulinum Neurotoxin Type A (BoNT A) Injection for Wrist, Elbow and Shoulder In order to capture the accurate representation of tremor in the upper limb, measurements were done on the entire arm on all major joints; wrist, elbow and shoulder. Wrist tremor is highly variable and has three directions of movement: flexion/extension (F/E), radial/ulnar (R/U), and pronation/supination (P/S), as mentioned in Example 1. Elbow tremor has one direction of movement done by flexion/extension (F/E), while shoulder tremor has three directions of movement: flexion/extension (F/E), abduction/adduction (A/A), and internal/external rotation. With same criteria as Example 1, 18 ET and 23 PD patients, different recruits from Example 1, were enrolled into a 8 month long arm tremor study with baseline data collected (Table 4).

TABLE 4

Subject Demography for ET and PD

| | ET | | | | PD | | |
|---|---|---|---|---|---|---|---|
| ID | Age | Gen | Side | ID | Age | Gen | Side |
| MT-07 | 76 | M | R | MT-01 | 71 | F | L |
| MT-08 | 74 | F | R | MT-02 | 35 | M | R |
| MT-09 | 66 | M | R | MT-03 | 62 | M | R |
| MT-10 | 76 | M | R | MT-04 | 79 | M | R |
| MT-11 | 77 | M | R | MT-05 | 53 | M | L |
| MT-14 | 82 | M | R | MT-12 | 60 | M | R |
| MT-22 | 62 | F | R | MT-15 | 59 | M | R |
| MT-27 | 69 | F | R | MT-16 | 77 | F | L |
| MT-43 | 61 | M | R | MT-18 | 62 | M | R |
| MT-44 | 80 | F | L | MT-20 | 66 | M | R |
| MT-47 | 68 | F | L | MT-23 | 76 | M | R |
| MT-50 | 85 | M | R | MT-24 | 52 | F | R |
| MT-51 | 50 | M | R | MT-30 | 62 | F | L |
| MT-53 | 66 | F | R | MT-33 | 47 | F | R |
| MT-56 | 63 | F | R | MT-37 | 80 | M | R |
| MT-57 | 79 | M | R | MT-40 | 59 | M | L |
| MT-58 | 79 | F | R | MT-42 | 69 | M | R |
| MT-59 | 60 | M | R | MT-45 | 70 | F | R |
| | | | | MT-46 | 68 | M | R |
| | | | | MT-48 | 70 | M | R |
| | | | | MT-49 | 69 | M | L |
| | | | | MT-52 | 80 | F | R |
| | | | | MT-54 | 66 | F | L |
| Avg | 70.722 | | | | 63.278 | | |
| SD | 9.097 | | | | 10.836 | | |

Figure 5A:
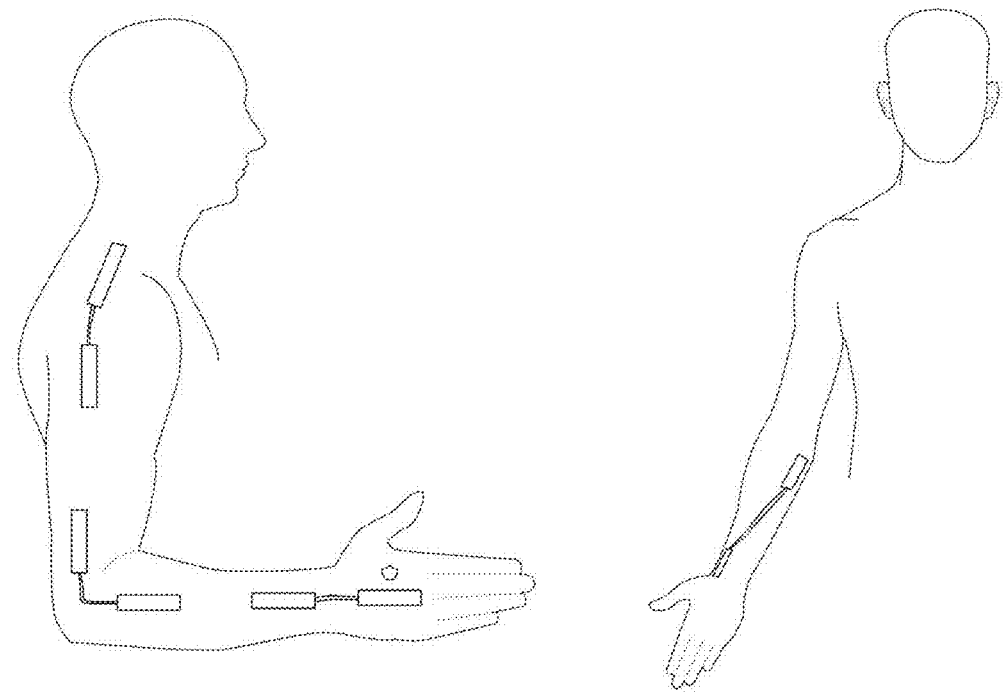
FIGS. 5A-D depict location of different sensors on dorsal surface of hand, wrist, elbow, forearm and shoulder of a subject for assessing tremor in the subject's arm.
Figure 5B:
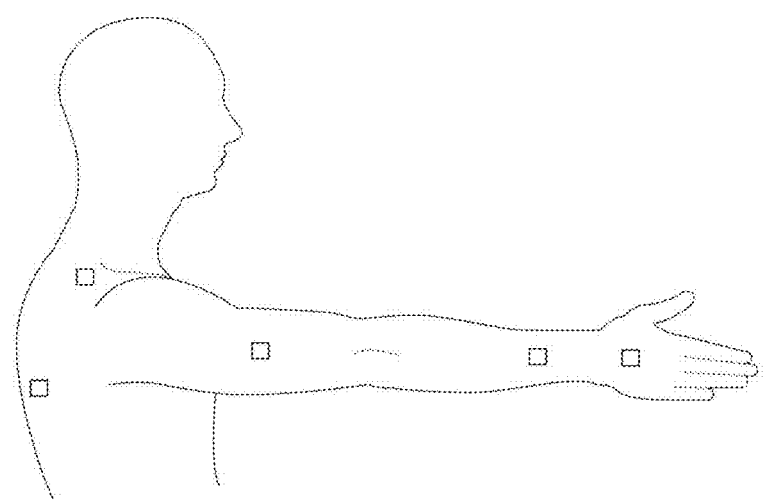
Figure 5C:
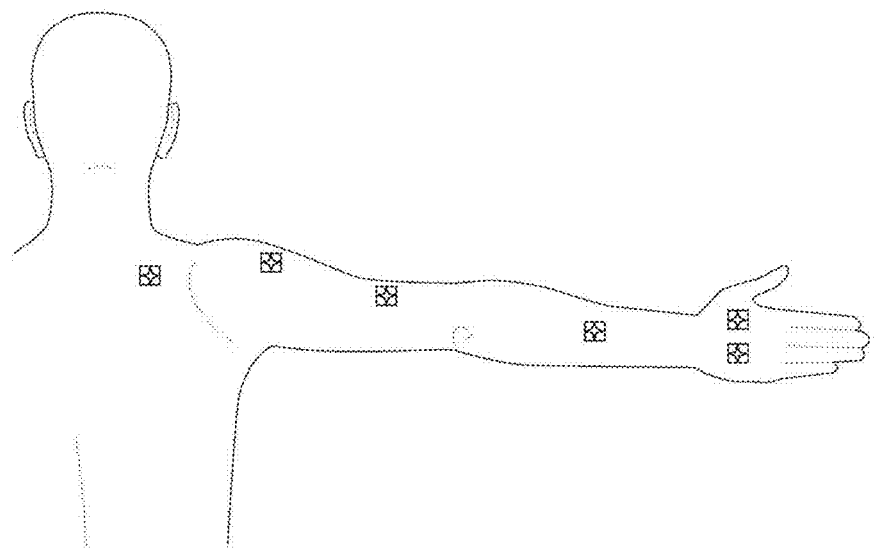
Figure 5D:
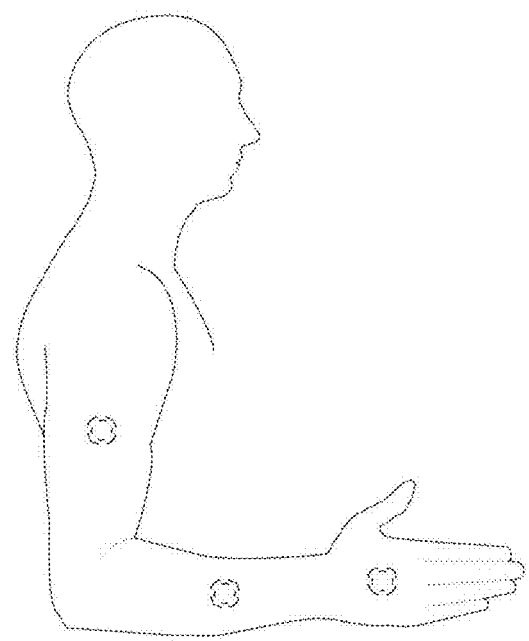

ID = participant's identification number
Gen = gender
Avg = average
SD = standard deviation Kinematic Methods Kinematic devices were used to record composition of wrist tremor, in addition to overall tremor amplitude/severity. Wrist flexion/extension (F/E) and radial/ulnar deviation (R/U) were measured using a twin flexible axis electro-goniometer (SG150, Biometrics Ltd) placed across the wrist joint. Forearm pronation/supination (P/S) was measured using a single flexible axis electro-torsiometer (Q150, Biometrics Ltd) placed along the inner forearm, parallel to the flexor carpi radialis. Together, the sensors provided 3 degrees of freedom (DOF) angular measurements at the wrist. Hand tremor was also recorded using a linear accelerometer (3D, 6 g, Noraxon®) on the hand giving three degrees of linear acceleration. A single flexible axis electro-goniometer was placed on the elbow joint to measure flexion/extension (F/E) and another twin axis electro-goniometer was placed on the shoulder joint to measure flexion/extension (F/E) and abduction/adduction (A/A). FIG. 5A illustrates unique placement of these sensors types for measuring wrist, elbow and shoulder tremors. A sensor placed diagonally across the wrist was particularly useful for collecting data on a full range of wrist motion.

All recordings were performed in the seated position with a similar PC interface as mentioned in Example 1. Calibration for wrist was also similar to the description found in Example 1 with the addition of calibration at the elbow and shoulders which was individually done by placing the elbow at neutral F/E, followed by neutral F/E and neutral A/A positions for shoulder. Subjects then performed a series of 7 tasks to measure tremor, first by placing the arm and hand relaxed and at rest on the patient's own lap (rest-1), and then resting the arm on support surface (rest-2). The hand may be turned with the palm facing the side to reduce gravitational influence on the tremor. To induce the tremor during rest-1 and rest-2, patients are asked to keep the recording arm relaxed while tasked to make grasping hand gesture with the non-recording arm to induce the tremor, and to distract the subject from the recording arm so that the recording arm is more likely to be relaxed. Then both arms and hands are positioned to extend outward in front parallel to the ground and palms facing the ground (post-1). Afterwards, both arms are placed in posture-neutral with again the arm and hand stretched outwards in front and the palms this time facing each other (posture-2). Patient is then asked to perform goal directed movement between nose and target (kinetic), previously mentioned in Example 1. Finally, the patient then holds an empty cup (no load) and holding a weighted cup (full load) on front of them while seated. All tasks are recorded each for 20 seconds in duration and are repeated a total of 3 times. All tasks but kinetic task were used in full arm tremor analysis.

Figure 6A:
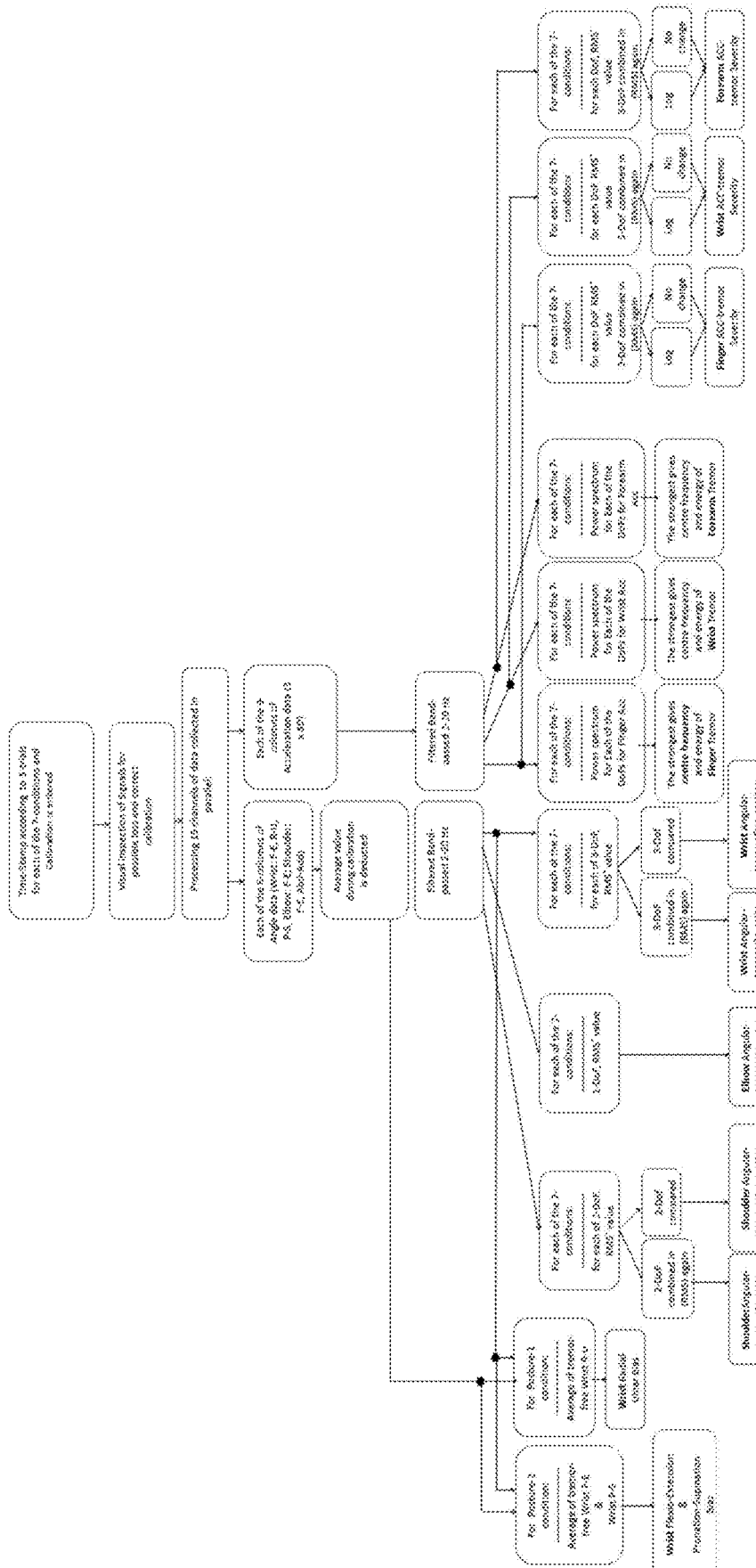
FIG. 6A depicts a flowchart showing how sensor data collected from the sensors in the sensor set up of FIG. 5A are used to obtain measures of tremor angle, severity and composition at each joint in an upper limb such as an arm.
Figure 6B:
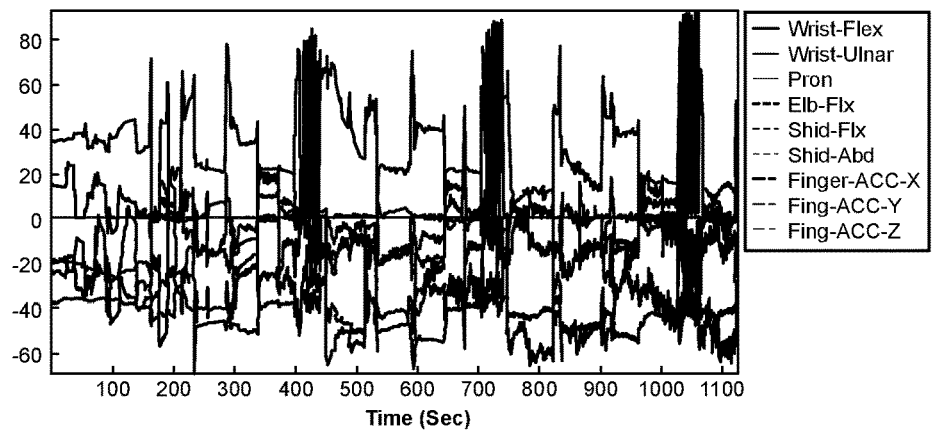
FIG. 6B shows a sample graph of the raw signal data following assessment with no data processing.
Figure 6C:
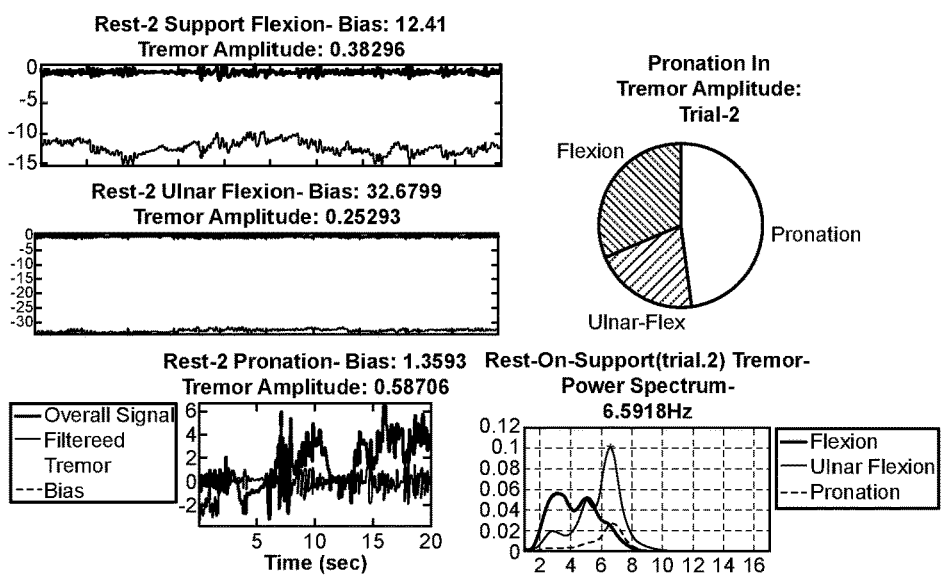
FIGS. 6C-6D show a 20 out of 1150 second sample of the raw tremor signal undergoing filter band pass along with preliminary composition analysis.
Figure 6D:
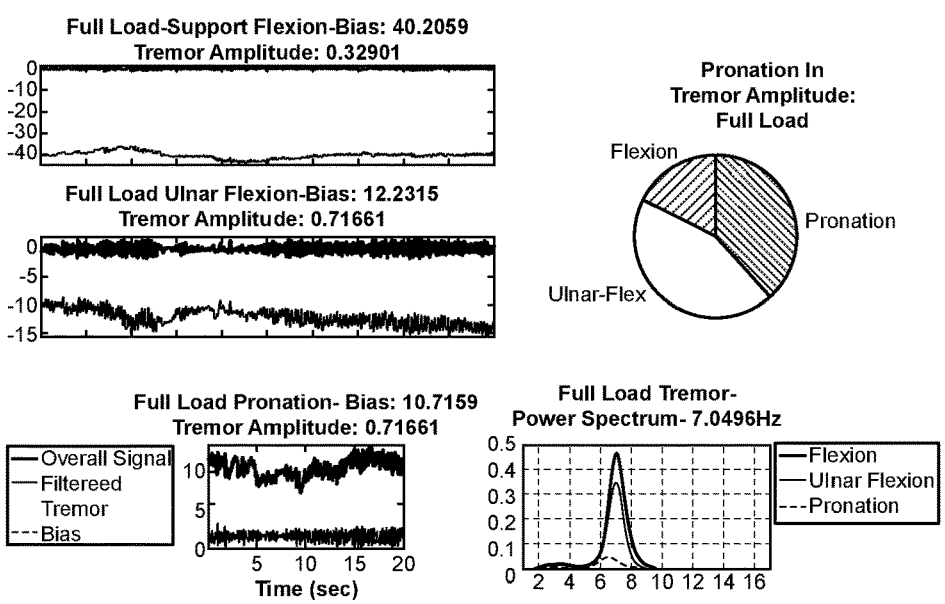
Figure 6E:
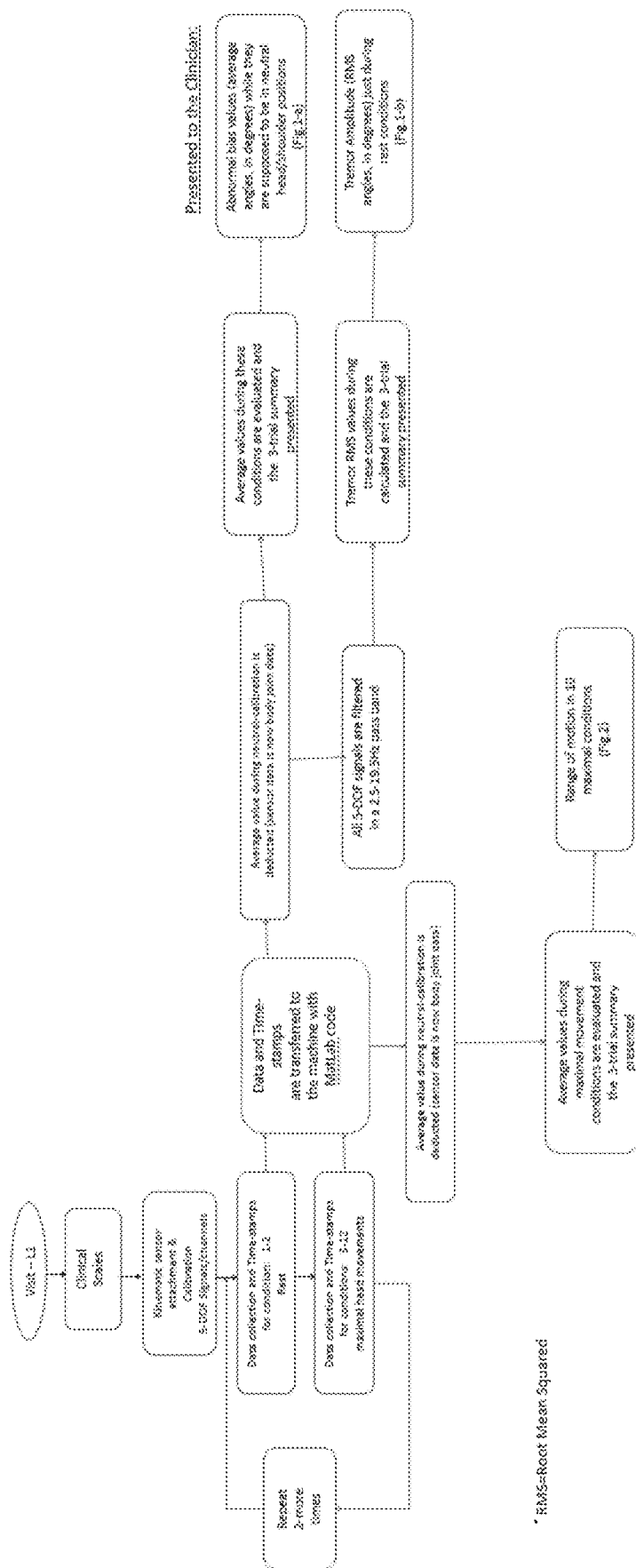
FIG. 6E depicts a flowchart showing how sensor data collected from sensors are used to obtain measures of tremor angle, severity and composition for neck and head.

Signal processing was performed in MatLab® (Math-Works, R2011a), similar to Example 1. For each subject data file, the segments corresponding to each trial were extracted for every task. Each segment included three angular position signals for the wrist, elbow and shoulder, and three linear acceleration signals for the hand. For each angular position signal, the mean value during neutral position calibration was subtracted before further processing. All tremor signals (both angular position and acceleration) were band-pass filtered (2-20 Hz, least-squared finite impulse response filter, order 2000). Signals were symmetrically padded on both ends. For each tremor signal, after filtering, root-mean-squared (RMS) value was calculated as the measure of amplitude to avoid filter transient effects. Amplitude for 3D hand tremor, amplitude for 3-components of wrist tremor, and directional bias of each component during trials were calculated for 3-trials of rest-1, rest-2 and for 3-trials of post-1, post-2 and for 3-trials for no load and full load. Three dimensions of linear acceleration at the hand were combined (RMS) to provide overall tremor severity. Percent contribution for each of the three components to wrist tremor was determined with respect to a combination of summed 3D angular amplitude (F/E, R/U, and P/S,) and one component at the wrist (F/E). Likewise, at the shoulder the percent contribution for the two components was determined for F/E and A/A. Directional bias for each of the components were calculated by averaging the signal, taking into account direction (positive=F/R/P; negative=E/U/S). Additionally, the bias at the wrist was further analyzed at the wrist during post-1 and post-2 to provide an indication to physician on information needed to determine if one group of antagonist muscles need to have greater consideration during treatment compared to another. This process is illustrated in FIGS. 6A, 6B and 6C.

Results

Following measurement and analysis of the subject's unique right arm tremor, the data was provided to a clinician for review. Based on the information, the total graphical values of each limb segment at the wrist, elbow and shoulder (FIG. 7A) were inspected. As seen in the fourth panel from the top in FIG. 7A, total tremor amplitudes for wrist, elbow and shoulder were 1.22, 0.12 and 0.1, respectively. A primary determination was then made of whether the maximal values at the wrist, elbow, and shoulder required treatment. Depending on the combination of limb segments that needed treatment, each limb segment was further reviewed based on the information displayed while the limb was captured at rest, during stretched out arm posture, action position, and when the arm was in various load positions (see fifth panel in FIG. 7A). Based on the positions of the limb at rest, posture, action, load or a combination of all arm positions, the maximal tremor amplitude can be determined.

Figure 7A:
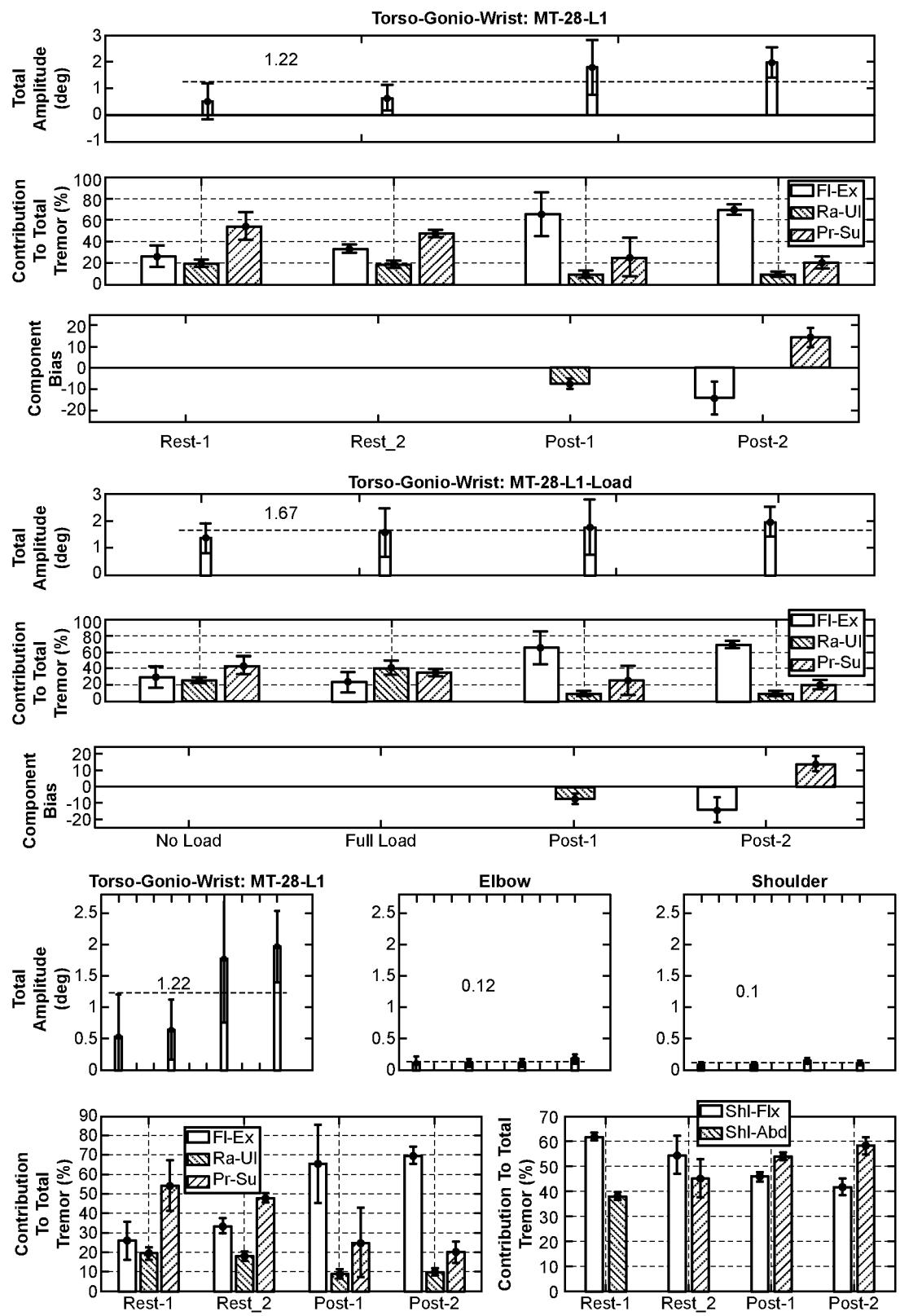
FIGS. 7A-B depict graphs showing muscle composition and directional bias for the right arm tremor assessed in the subject in the sensor setup of FIG. 5A before (FIG. 7A) and after (FIG. 7B) treatment with Botulinum neurotoxin type A (BoNT A) injection therapy.
Figure 7B:
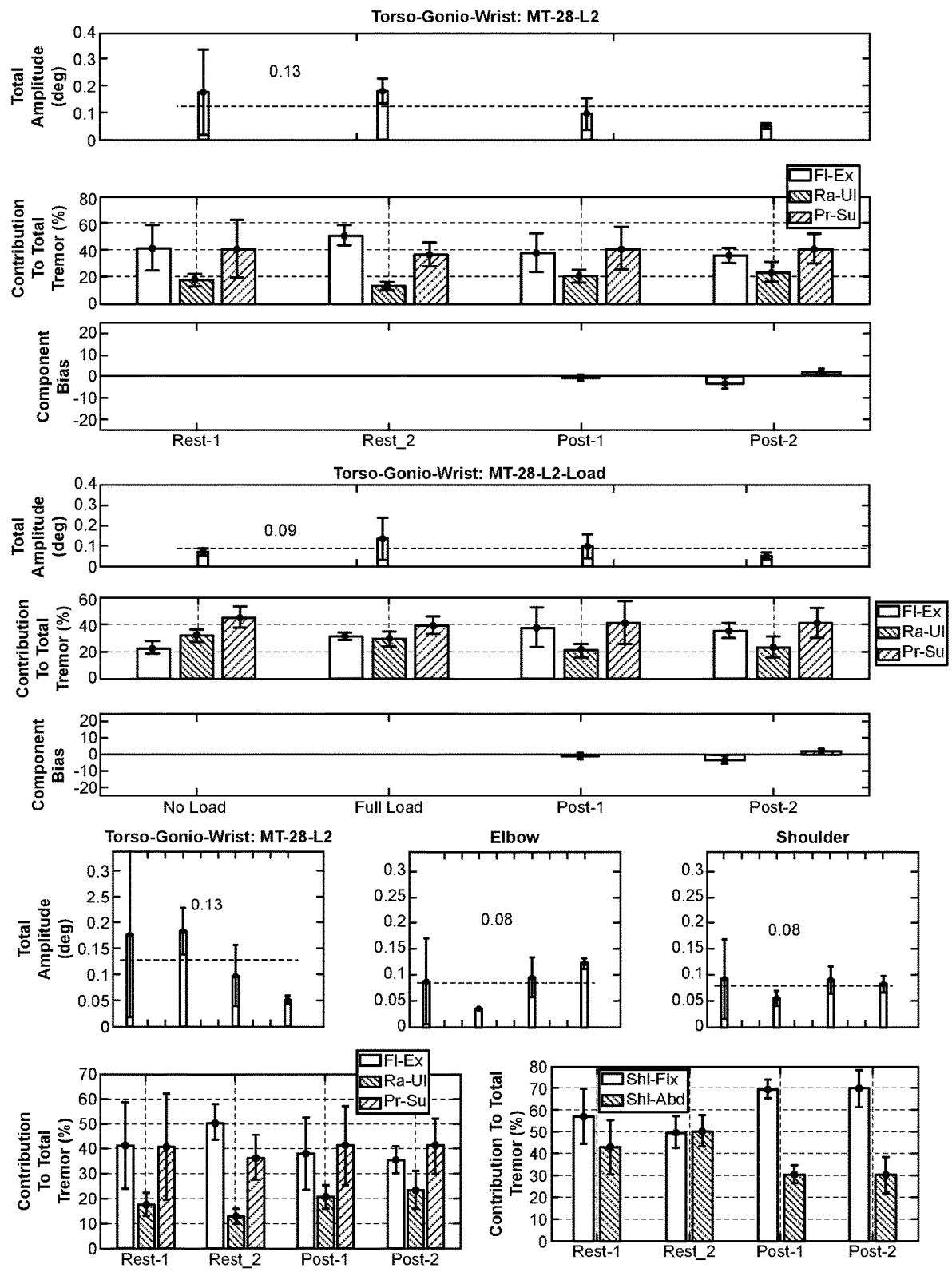
Figure 7C:
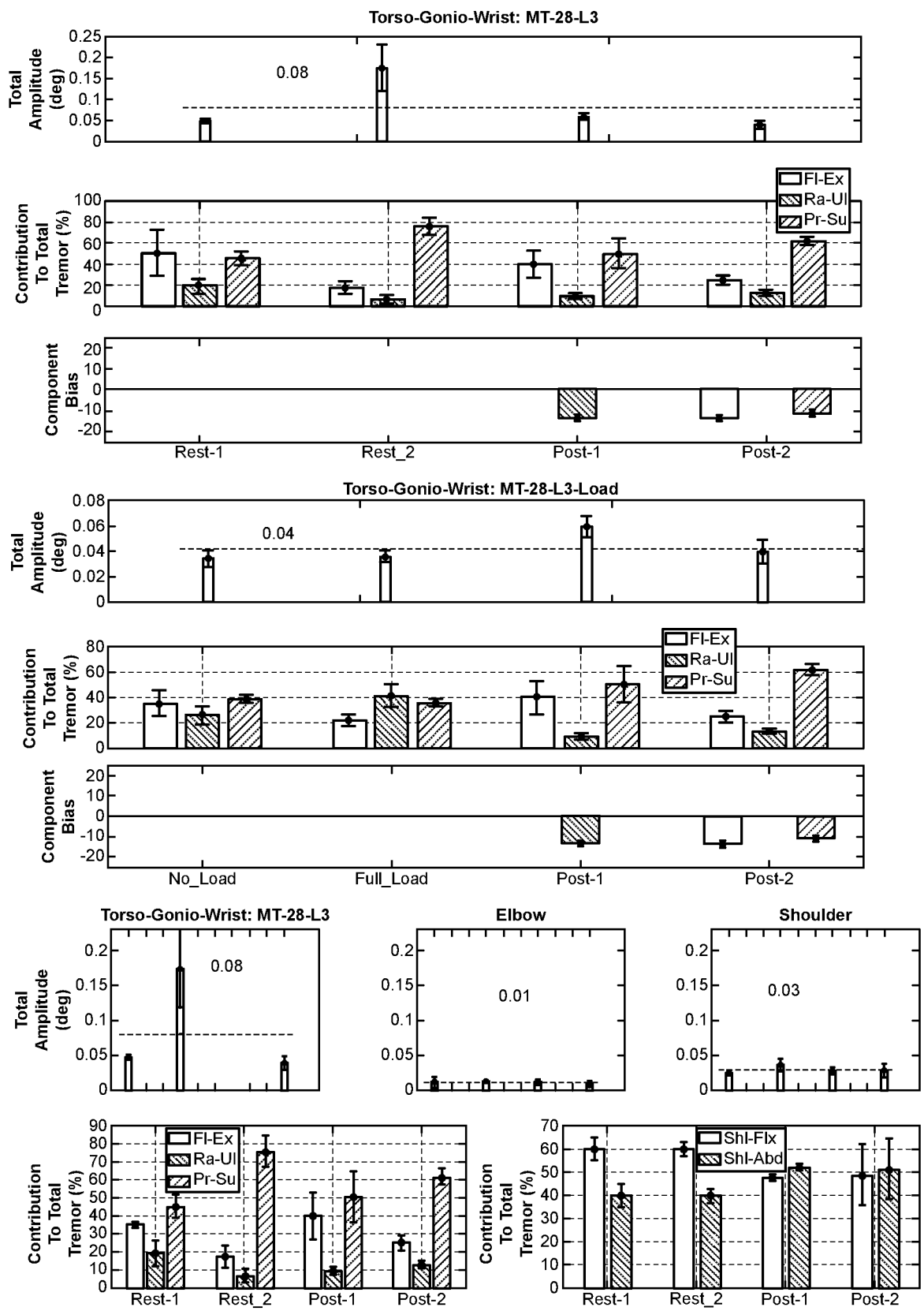
FIG. 7C shows muscle composition and directional bias measured at the time of the next injection visit.
Figure 8A:
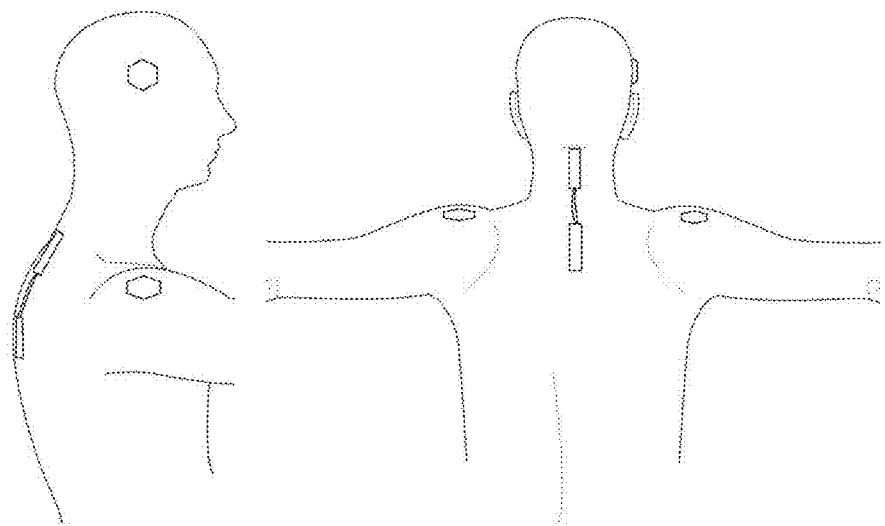
FIGS. 8A-D depict location of different sensors on head, neck and shoulder of a subject for assessing tremor and dystonia in the subject's neck and head.
Figure 8B:
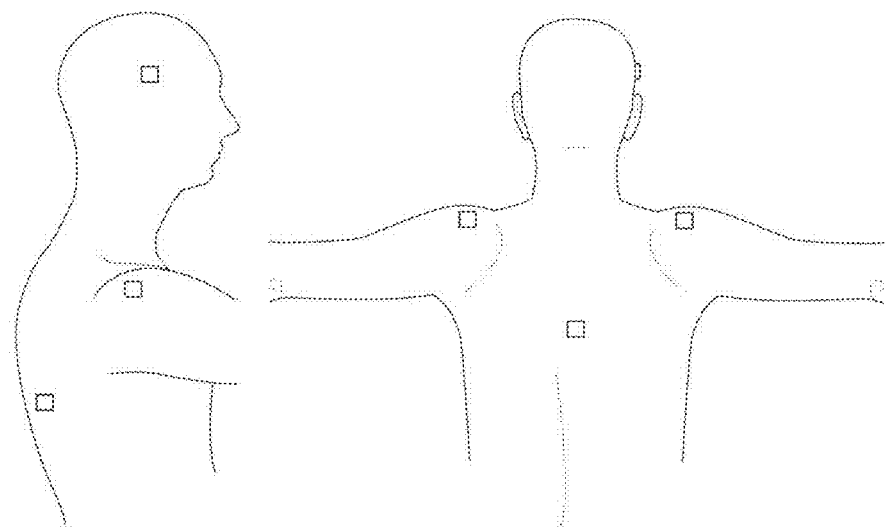
Figure 8C:
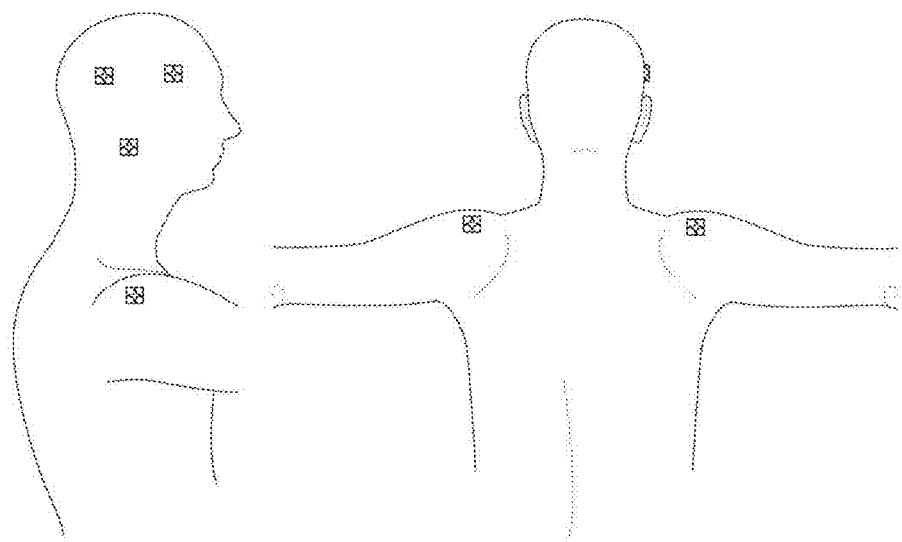
Figure 8D:
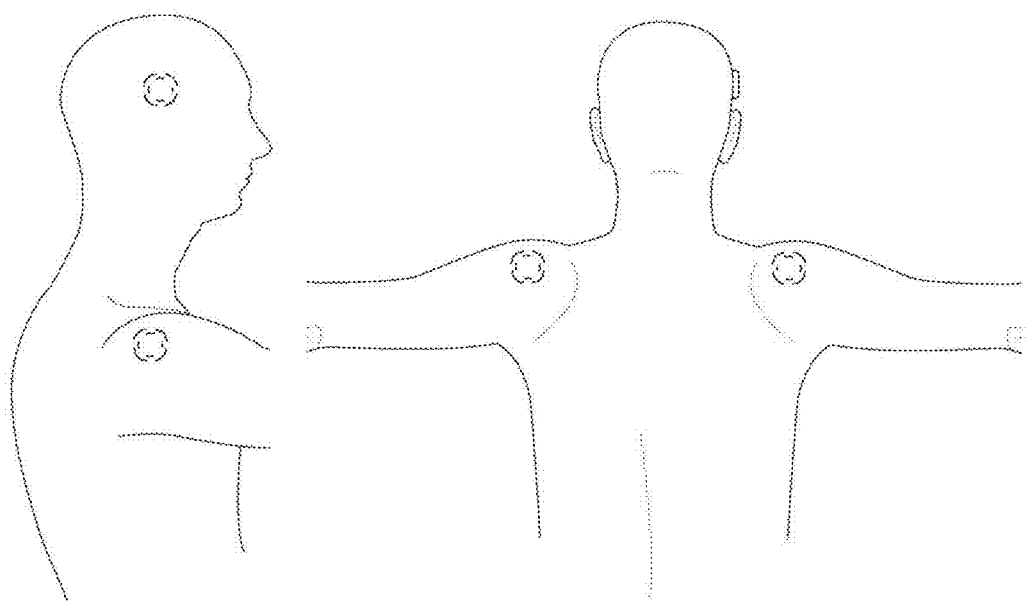

For the wrist, the maximum tremor amplitude is 1.22 as shown in the first panel in FIG. 7A. From the tremor amplitude at the wrist during rest and load, the graphed results are correlated to the sub-movements flexion-extension (F/E) and radial-ulnar (R/U) (see second panel in FIG. 7A). The tremor amplitudes relating to (F/E) and (R/U) wrist movements help the clinical evaluation of the severity of deviation/bias the wrist has from a neutral/normal position (see third panel in FIG. 7A). The maximal amplitudes at these two sub-movements are then ranked from the top two arm postures in terms of priority of concern at the wrist. Based on the final composition at the wrist, consisting of wrist deviation (directional bias) and tremor amplitudes for F/E and R/U during rest, posture and load, a dosing paradigm as well as selection of which muscles for injection may be determined.

For the elbow, the tremor amplitude (0.12 as seen in the first panel of FIG. 7A) was found to be clinically significant. The pronation-supination (P/S) and radial-ulnar (R/U) sub-movements at the elbow were assessed separately. The clinician was fully aware during the kinematic assessment that the measured tremors at the elbow have contributions to the wrist movements as well being influenced by the biceps. Based on the elbow composition, equal amounts would be injected at the elbow muscles; however, if supination deviation/bias was significant, additional dosing of medication would be given at the bicep. This makes injection at the elbow different for elbow flexor compared to extension as the elbow flexion does supinate.

At the shoulder the sub-movements were identified as flexion-extension (F/E) and abduction-adduction (A/A). The relative tremor amplitude at each sub-movement was considered separately. It was determined whether one or both of F/E and A/A are selected as contributors to tremor by considering flexion and/or extension, abduction and/or adduction as individual sub-movements.

At each joint, the amplitude, composition and directional bias of tremor then permitted selection of dosage and location of injection. Based on the information provided, the muscles selected for injection could be taken from the following list: flexor carpi radialis, flexor carpi ulnaris, brachioradialis, extensor carpi radialis, extensor carpi ulnaris, pronator teres, pronator quadratus, supinator, biceps, pectoralis, teres major, triceps, deltoids, supraspinatus, and infraspinatus. In this example, flexor carpi radialis, flexor carpi ulnaris, extensor carpi radialis, extensor carpi ulnaris, pronator teres, pronator quadratus, biceps, pectoralis, triceps, and supraspinatus were selected for BoNT A injection.

The subject had a follow-up assessment 6 weeks after initial injection of BoNT A. Both the clinician and patient saw significant improvement in hand and arm function following the treatment. Kinematic values (see FIG. 7B) show significant decrease in total tremor amplitudes in the wrist, elbow and shoulder. Comparing FIG. 7A to FIG. 7B, it can be seen that tremor amplitude at the wrist was reduced from 1.22 to 0.13, at the elbow was reduced from 0.12 to 0.08 and at the shoulder was reduced from 0.1 to 0.08. Wrist deviation does not appear to be a major contributor and seems to have returned to normal.

Example 3: Treating Head and Neck Tremor with Torticollis Using Kinematic Analysis and Botulinum Neurotoxin Type A (BoNT A) Injection A subject's head and neck tremor was measured and analyzed generally in accordance with the kinematic method described in Examples 1 and 2. To accomplish this, sensors were placed on the subject's body as depicted in FIG. 8A, with sensors on the head and neck of the subject. FIG. 8A depicts sensors on the head, shoulder and neck. The torsiometer was placed at the back of the neck while two inclinometers are placed on both shoulders and one inclinometer is placed on the side of the patient's head. The torsiometer was able to detect rotational tremor and dystonic movements along with the rotational range of movement. The two inclinometers on the shoulders are able to capture shoulder elevation. The inclinometer located on the side of the patient's head was used to measure tremor and dystonic movements for lateral left-right tilts and forward-backward head sagittal tilt. This same inclinometer on the head was also able to record the range of motion for caput and collis head movements during lateral left-right tilts and forward-backward sagittal tilt. Patients were positioned in calibration positions prior to each kinematic recording by adjusting the patient's head to neutral position with minimal rotational, lateral tilt and forward-backward sagittal tilt. The head is also gently held still to prevent tremor and dystonic movements during calibration. The assessment involves 12 tasks. The first assessment was done by asking the patient to look forward while in a seated position and to keep the head and neck as relaxed as possible without inhibiting any involuntary movements. The first task is important for determining the head positional bias when the patient typically looks forward. Then for task two the patient was asked to close their eyes in the same relaxed position. The third and fourth tasks asked the patient to rotate their head as far left and then as for right as they can. The fifth to eighth tasks involved having the patient with their eyes opened position their head tilted upwards in caput and collis positions, followed by caput and collis positions with head tilted downward. The last four tasks required the patient to tilt their head to the left and right side in again caput and collis positions. All tasks are performed at least for 3 trials.

During the entire assessment, 3 degrees of freedom are recorded for lateral tilt, sagittal tilt, and axial rotation, and 2 degrees of freedom for shoulder angular elevation. The average values during calibration for each degree of freedom are calculated and are used as reference point for comparison with other tasks the patient performs. For each of the 5 signals, the signal goes through a band-pass filter, then the average amplitude of tremor during tasks one and two (Rest Eye-open, Rest-Eyes-Closed) are calculated for all three trials to be displayed as a boxplot. The data analyzed and provided to the physician are one of three types of graphs. The first graph shows the abnormal bias values while the head is supported in a neutral position, relaxed and not resisting any tremor or dystonic movements. The second graph shows the tremor amplitude (RMS angles, in degrees) just during rest condition with eyes open and closed. The third graph shows the range of motion of the neck and head during task performance. This process is illustrated in FIG. 6E.

Following measurement and analysis of the subject's head and neck tremor, the data was provided to a clinician for review. First, whether treatment is needed was assessed at each of the three primary positions, which are lateral tilt, rotational, and sagittal motions based on the kinematic values. These three primary positional kinematic values represent the deviation away from normal head position, which should have a value of zero. Shoulder rise-drop is also examined to determine if treatment is required.

As seen in FIG. 9A, the kinematic results show the need to further assess tilt, rotational and sagittal kinematic value.

Figure 9A:
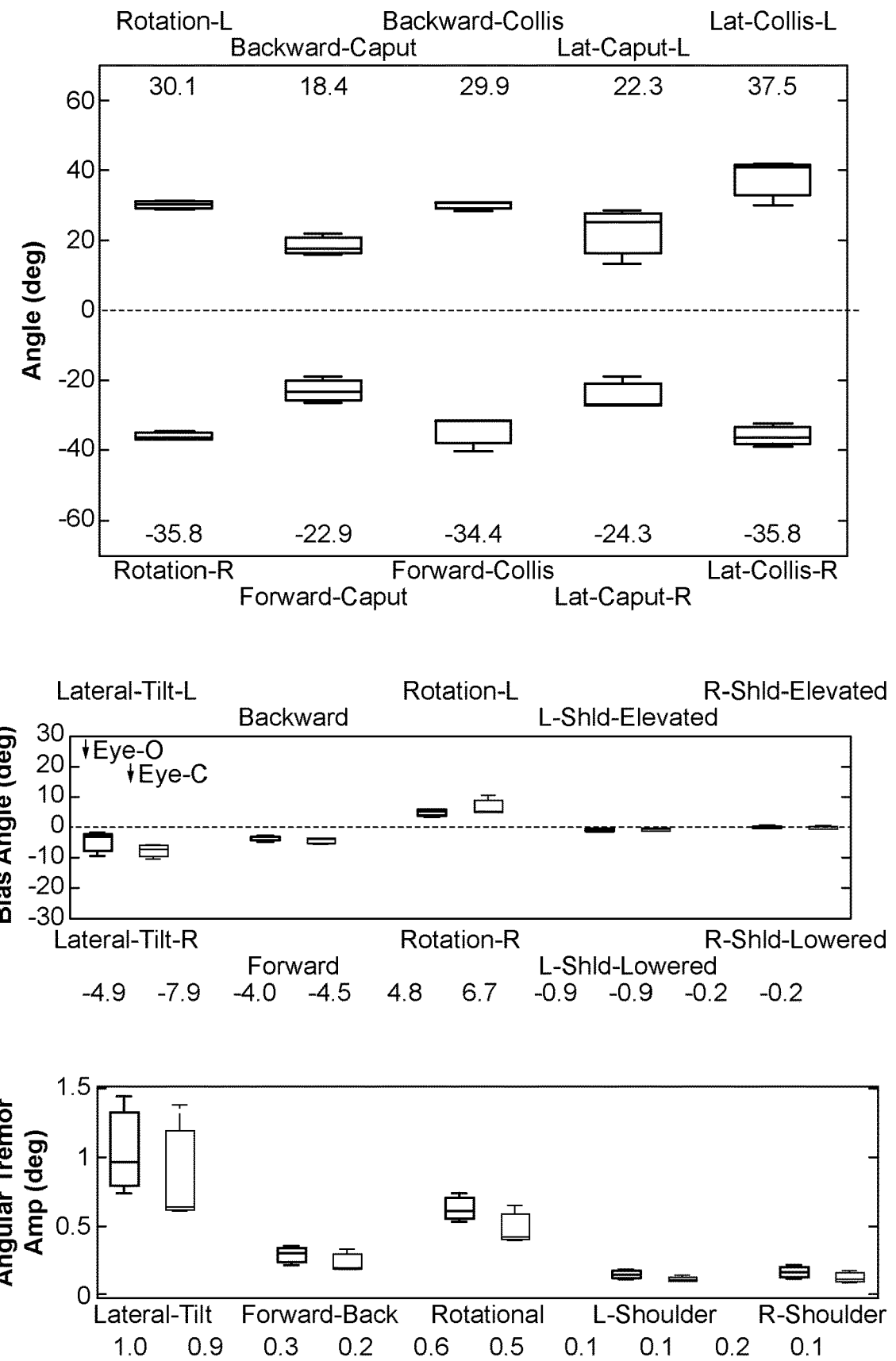
FIGS. 9A-B depict graphs showing head and neck movement data for the head and neck tremor assessed in the subject of FIG. 8A before (FIG. 9A) and after (FIG. 9B) treatment with Botulinum neurotoxin type A (BoNT A) injection therapy.

The individual kinematics recordings for each motion are also assessed for difference between eyes open (Eye-O) and eyes closed (Eye-C) (see top panel in FIG. 9A). Based on the kinematic values, it is evident that the subject has head posture deviation of tilting the head to the right. The kinematic values also show the subject's head has a forward tilt (chin downward) and a head rotation to the left.

Now that abnormal head posture has been determined, further assessment for tremor angular amplitude in each primary position is done. The kinematic data (FIG. 9A, second panel) shows most tremor in the tilt motion, followed by rotational motion and lastly the sagittal forward-backward motion. With both head deviation and tremor contributions assessed, the subject's range of neck motion is assessed from the kinematic data (FIG. 9A, third panel) to assess movement abnormalities.

A dosing table is constructed and muscles needed for injection selected to help correct for head posture, tremor and possible range of motion problems. Based on the information provided, the right and/or left muscles selected for injection could be taken from the following list: semispinalis capitis, splenius capitis, trapezius, levator scapulae, sternocleidomastoid, scalene muscles, splenius cervicalis, and longissimus capitis. In this example, the right and left splenius capitis, right and left sternocleidomastoid, and right levator scapulae were selected for BoNT A injections.

Figure 9B:
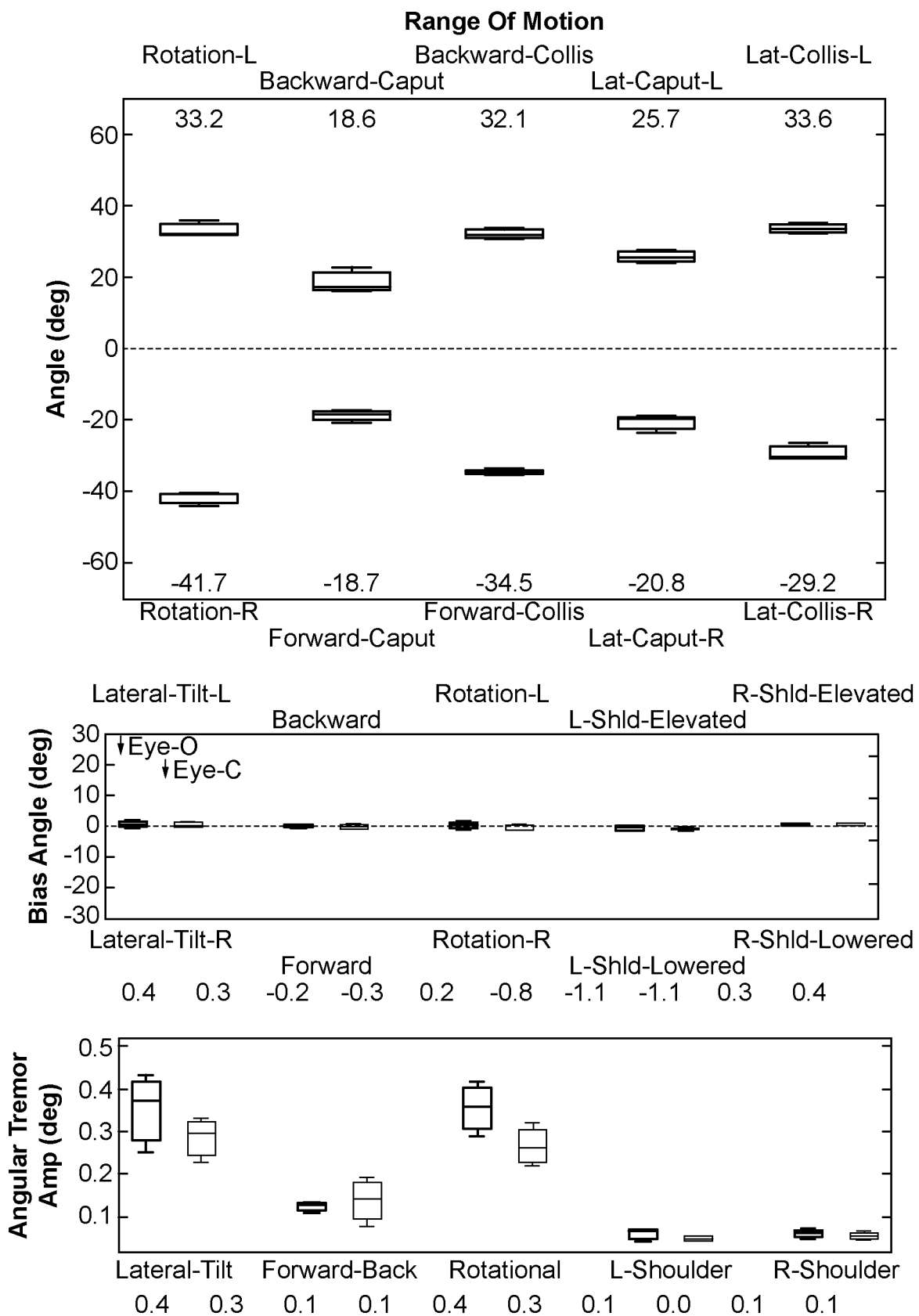

The subject had a follow-up assessment 6 weeks after initial injection of BoNT A. Both the clinician and patient saw significant improvement in head posture, along with a decrease in head tremor. Kinematic values (FIG. 9B) show significant decrease in total tremor amplitudes motions involving lateral tilt, sagittal tilt and rotation (see the first panel of FIG. 9B compared to the first panel of FIG. 9A). The kinematic results also show improvement in the patient's overall range of motion following treatment.

Example 4: Determining Botulinum Neurotoxin Type A (BoNT A) Injection Dosages and Muscle Selection Using Data from Kinematic Analysis Prior to the present invention, dosage regimes were based solely on the severity of the tremor, which informed a total dosage of drug but provided no guidance on how to divide the total dosage between the muscle groups and individual muscles. Without accurate information about composition and directional bias, the total dosage was divided between muscle groups and muscles based entirely on the judgement and experience of the clinician. In the present invention, accurate information about muscle group composition and directional bias permits greater accuracy and consistency in making recommendations for dividing the total dose appropriately. Especially since directional bias in a tremor can now be determined, the amount of drug to be injected into a particular muscle can be more accurately determined.

The total dosage of the drug to inject into the muscles of a particular joint is informed by the severity of the tremor at that joint, which is indicated by the amplitude of the tremor. The amplitude may expressed in any units, for example angular displacement or the average of the root mean square (RMS) of each degree of freedom of the tremor, provided the correlation is made consistently. Total mean angular amplitude in degrees from 0° may be determined from the mean amplitudes for each muscle group involved in the tremor (e.g. F/E, R/U and P/S). The total dosage for a joint may be determined from a standard curve of dosage vs. tremor amplitude for that joint, or from a rating scale correlating a range of amplitudes to a range of total dosages, or from physician experience in correlating amplitude to total dosage. In some cases, the total maximum dosage may be proscribed by external factors, such as inclusion criteria for controlled studies and drug costs.

Once the total dosage is determined, the total dosage may be divided between the muscle groups based on the relative contribution of each muscle group to the tremor. The dosage given to each muscle may then be determined from directional bias within each muscle group on the basis of the relative bias detected by the sensors.

In this example, Botulinum neurotoxin type A (BoNT A) injection dosage and placement decisions are made from sensor data collected for amplitude, composition, and directional bias of joint movement of an essential tremor (ET) subject. A similar procedure may be followed for other types of tremors, for example tremors in subjects with Parkinson's disease.

Figure 10A:
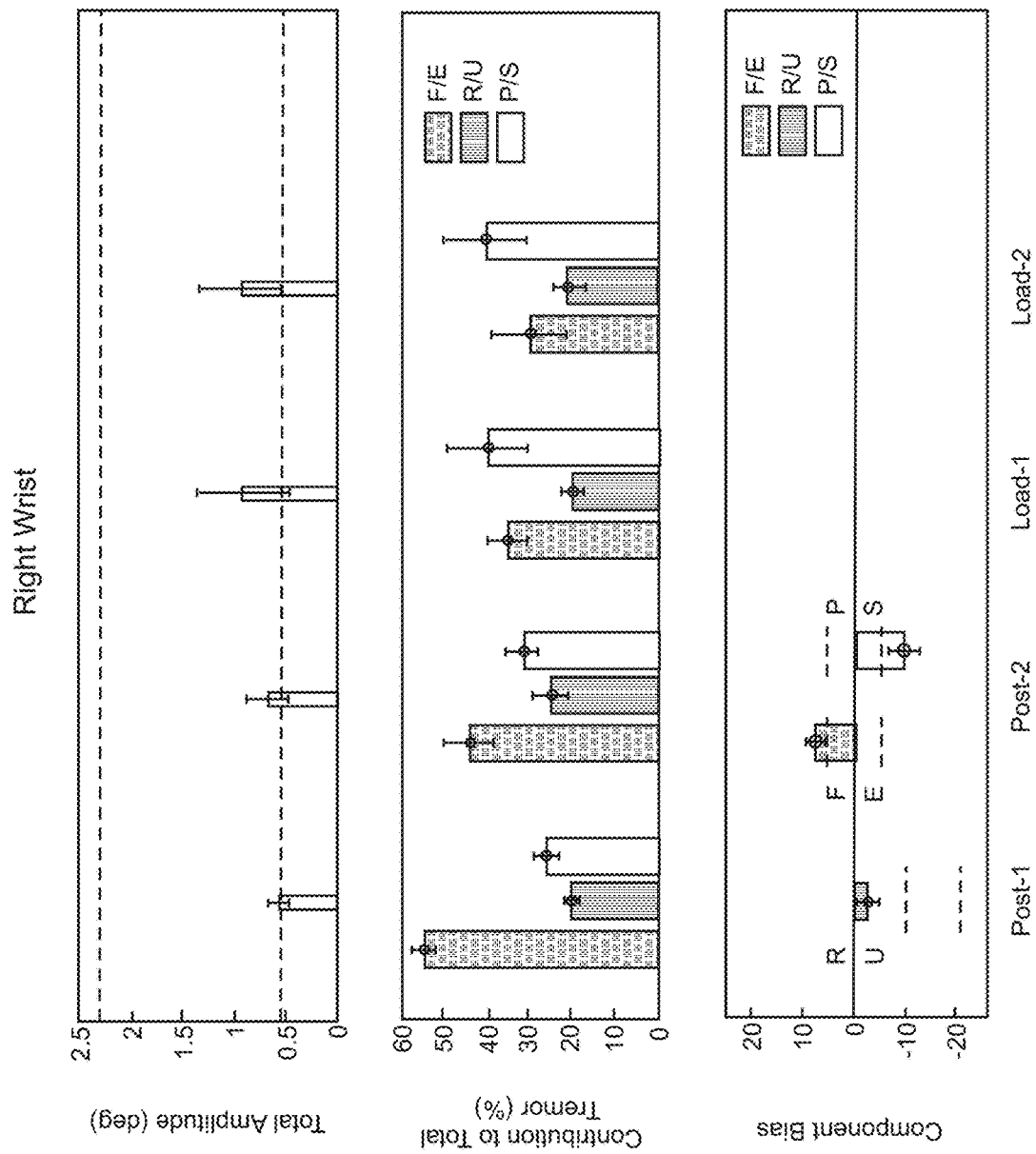
FIGS. 10A-C show graphs summarizing sensor data collected for amplitude, composition, and directional bias of joint movement of an essential tremor (ET) subject's right arm, including wrist movement (FIG. 10A), elbow movement (FIG. 10B) and shoulder movement (FIG. 10C).
Figure 10B:
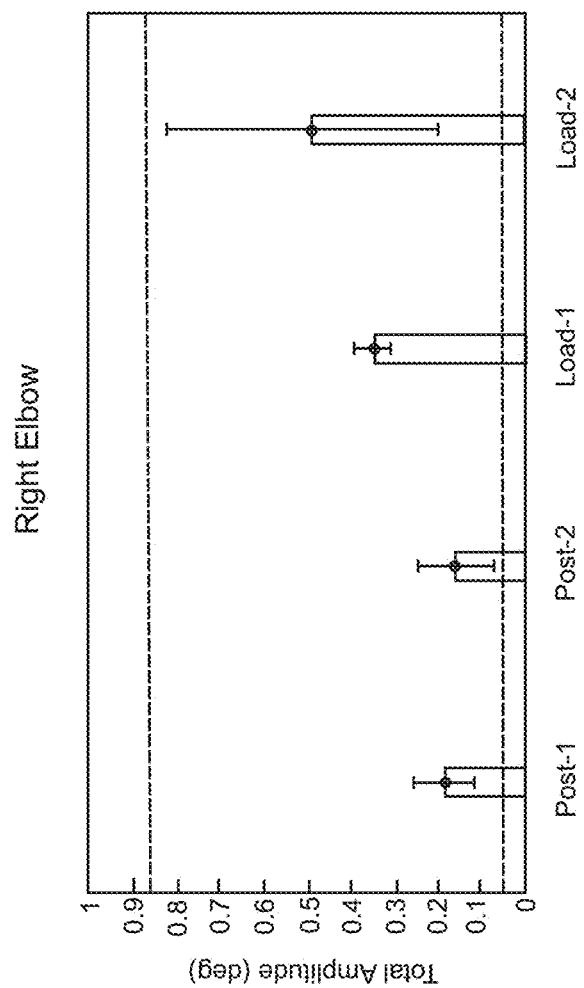
Figure 10C:
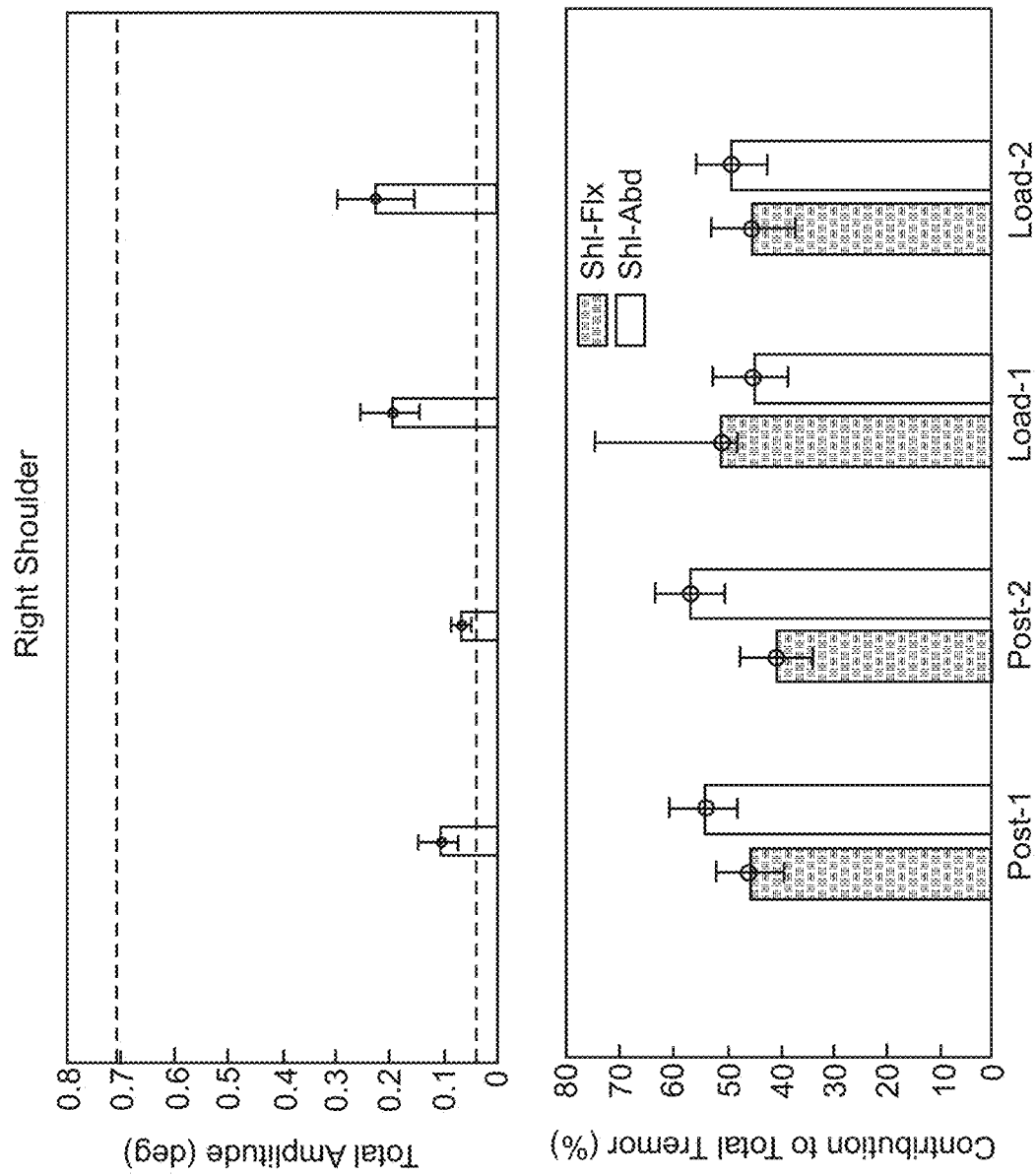

Kinematic data was collected on the right arm of an essential tremor (ET) subject during a tremor event using the sensor system depicted in FIG. 1. Graphs summarizing the kinematic data from the sensors were prepared for wrist joint movement (FIG. 10A), elbow joint movement (FIG. 10B) and shoulder joint movement (FIG. 10C). FIG. 10A provides data for the wrist joint including total amplitude (upper graph), composition (i.e. contribution of muscle groups to total tremor) (middle graph) and directional bias within each muscle group (lower graph). FIG. 10B provides total amplitude data for the elbow joint. FIG. 10C provides data for the shoulder joint including total amplitude (upper graph) and composition (i.e. contribution of muscle groups to total tremor) (lower graph). Directional bias data was not graphed for the shoulder joint and it was assumed that there was no directional bias in the shoulder movements. The data collected for each joint was obtained for a series of four postural tasks: Post-1, Post-2, Load-1 and Load-2. The postural tasks Post-1 and Post-2 are described above. Load-1 involves the subject holding an empty cup with the arm bent 90-degrees at the elbow. Load-2 is like Load-1 except that the cup is full. If the subject had Parkinson's Disease rather than Essential Tremor, data from two more postural tasks (i.e. Rest-1 and Rest-2) would also be collected.

The subject was part of an overall study. The study proscribed inclusion criteria for treatment including maximum doses of BoNT A that could be administered to particular joints. Since doses are related to tremor amplitude, maximum and minimum amplitudes of joint movement were proscribed for each joint. Movements lower than the minimum or higher than the maximum were not treated. The dotted lines in the total amplitude graphs show the maximum and minimum amplitudes that were used to identify which subjects were within the exclusion criteria. In practice outside of controlled studies, a clinician is free to ignore such limits.

Table 5 below provides a summary of the particular muscles involved in movements at each of these joints, and therefore the muscles to be targeted for BoNT A therapy.

TABLE 5

| Joint | Target Muscles | Movement Composition |
| --- | --- | --- |
| Shoulder | M. pectoralis major (Pect. Maj.) | adduction, flexion |
|  | M. teres major (Tares Maj.) | extension |
|  | M. deltoideus (M. Delt.) | abduction |
|  | M. supraspinatus (M. supra) | abduction |
| Elbow | M. biceps brachii (Bicep) | flexion |
|  | M. triceps brachii (Tricep) | extension |

TABLE 5-continued

| Joint | Target Muscles | Movement Composition |
|---|---|---|
| Wrist | M. flexor carpi radialis (FCR) | flexion, radial deviation |
|  | M. flexor carpi ulnaris (FCU) | flexion, ulnar deviation |
|  | M. extensor carpi radialis (ECR) | extension, radial deviation |
|  | M. extensor carpi ulnaris (ECU) | extension, ulnar deviation |
|  | M. pronator teres (PT) | pronation |
|  | M. pronator quadratus (PQ) | pronation |
|  | M. supinator (Sup) | supination |

Wrist:

With respect to the wrist, the upper graph in FIG. 10A shows the amplitude of the tremor at the wrist in the series of four postural tasks: Post-1, Post-2, Load-1 and Load-2. To determine the amplitude of the tremor, the clinician must first select the postural task or tasks on which to base the determination. The postural task with the highest tremor amplitude or variability is normally selected, although the clinician is free to select a different task if the subject perceives a particular task to be the most bothersome, or may use an average over all or some of the tasks. Where two or more tasks have similar amplitudes, Load tasks take priority of Posture tasks and Load-2 task takes priority over Load-1 task. In the top graph of FIG. 10A, Load-2 is the task to select to determine total amplitude. In cases where the amplitude of at least two of the tasks is below the minimum amplitude for inclusion, the clinician must decide whether the joint would be injected at all.

To select total dose for the wrist based on the Load-2 data from the upper graph of FIG. 10A, a correlation chart is consulted for the wrist joint. In this case, amplitude is divided into four substantially equal ranges between the proscribed maximum (2.31°) and minimum (0.58°) limits, and dosages in increments of 10 units are correlated to the four ranges as follows: if total amplitude is 1.89°-2.31° then 60 units; if total amplitude is 1.46°-1.88° then 50 units; if total amplitude is 1.02°-1.45° then 40 units; if total amplitude is 0.58°-1.01° then 30 units. Since the total amplitude of the Load-2 task was in the 0.58°-1.01° range, the total wrist dosage is set at 30 units.

To determine how the total dosage is divided between muscle groups, the contribution of each muscle group to the total tremor as shown in the middle graph of FIG. 10A is examined for each task. For Post-1 the contributions are about 55% F/E, 20% R/U and 25% P/S. For Post-2 the contributions are about 45% F/E, 25% R/U and 30% P/S. For Load-1 the contributions are about 37% F/E, 20% R/U and 43% P/S. For Load-2 the contributions are about 34% F/E, 23% R/U and 43% P/S. The data from one or more of the tasks is selected, and the selection may be based on the clinicians experience or an average may be taken. In this case, the average across the tasks is taken and the average contributions of each muscle group are: 42.5% F/E; 22% R/U; and 35.5% P/S. Since the total dosage given to the wrist is 30 units, the F/E group would receive 12.75 units, the R/U group would receive 6.6 units and the P/S group would receive 10.65 units.

To determine the dosage of BoNT A to inject in each individual wrist muscle, the bottom graph in FIG. 10A showing directional bias (i.e. deviation from normal position) is examined. In examining the bottom graph in FIG. 10, it should be noted that Post-1 and Post-2 tasks focus on different degrees of freedom that are not counteracted by gravity. Therefore, in Post-1, ulnar deviation is expected to be between −10° and −20°. In Post-2, F/E and S/P posturing is expected to be between −+5° and −5°. The expected deviations are shown in dotted lines.

The Post-1 data shows a deviation in the radial direction of −10° away from the expected ulnar position, equating to a change in bias of 20% (10% per 5° deviation). Thus, within the R/U muscle group, 70% of the movement is due to radial muscles and 30% due to ulnar muscles. Since the R/U muscle group is to receive 6.6 units of the total dosage, 4.6 units should go to radial muscles (FCR, ECR) and 2 units should go to ulnar muscles (FCU, ECU).

The Post-2 data in the bottom graph in FIG. 10A shows a deviation in the flexion direction of 2.5° away from the expected flexion range, equating to a change in bias of 5% (10% per 5° deviation). This is less than 10% and is considered insignificant, therefore both flexion and extension muscles contribute equally to the contribution of the F/E muscle group. Since the F/E muscle group is to receive 12.75 units of the total dosage, 6.375 units should go to flexion muscles (FCR, FCU) and 6.375 units should go to extension muscles (ECR, ECU).

The Post-2 data in the bottom graph in FIG. 10A also shows a deviation in the supination direction of 5° away from the expected supination range, equating to a change in bias of 10% (10% per 5° deviation). Thus, within the S/P muscle group, 60% of the movement is due to pronation muscles and 40% due to supination muscles. Since the S/P muscle group is to receive 10.65 units of the total dosage, 6.39 units should go to pronation muscles (PT, PQ) and 4.26 units should go to supination muscles (Sup).

From Table 5, it is evident that several muscles receive dosage amounts stemming from more than one muscle group analysis. For example, the FCR will receive a dosage based on the dose calculated for the flexion muscles and the dose calculated for the radial muscles. The doses for the different aspects of the muscle groups are therefore divided equally between all the muscles having that aspect (e.g. flexion) and added to the doses calculated after a similar division among other aspects (e.g. radial). A similar analysis can be done for each muscle to produce a table as shown in Table 6 to arrive at the amount of BoNT A to inject into each wrist muscle.

TABLE 6

| Muscle | F | E | P | S | R | U | Units per Muscle |
|---|---|---|---|---|---|---|---|
| FCR | 3.1875 | 0 | 0 | 0 | 2.3 | 0 | 5.4875 |
| FCU | 3.1875 | 0 | 0 | 0 | 0 | 1 | 4.1875 |
| ECR | 0 | 3.1875 | 0 | 0 | 2.3 | 0 | 5.4875 |
| ECU | 0 | 3.1875 | 0 | 0 | 0 | 1 | 4.1875 |
| PT | 0 | 0 | 3.195 | 0 | 0 | 0 | 3.195 |
| PQ | 0 | 0 | 3.195 | 0 | 0 | 0 | 3.195 |
| Sup | 0 | 0 | 0 | 1.26 | 0 | 0 | 1.26 |

In an added complexity, the bicep muscle (M. biceps brachii) is also implicated in supination in the wrist. Therefore, more BoNT A should be injected into the Supinator muscle than indicated by this analysis. Further, because BoNT A is available only in discrete unit sizes, 5 units is typically the minimum that would be injected into any one wrist muscle when an injection is indicated, and the results of the calculation should be rounded to the nearest 5 units. From Table 6, it is therefore apparent in light of the foregoing that each wrist muscle would receive 5 units of the BoNT A for a total of 35 units to the wrist joint.

In this example, a combination of lower tremor severity and rounding dosages to the nearest 5 units resulted in the calculation indicating that all wrists muscles would receive 5 units. However, keeping the component contributions and directional bias the same but increasing tremor severity to an amplitude of 2.0 would have increased the total dosage to 60 units. With a total of 60 units for the wrist, the units per muscle in Table 6 would be doubled and with rounding to the nearest 5 units each muscle would receive a dosage of BoNT A as follows: FCR=10 U; FCU=10 U; ECR=10 U, ECU=10 U; PT=5 U; PQ=5 U; Sup=5 U.

Elbow:

With respect to the elbow, the graph in FIG. 10B shows the amplitude of the tremor at the elbow in the series of four postural tasks: Post-1, Post-2, Load-1 and Load-2. The postural task with the highest tremor amplitude or variability is normally selected, although the clinician is free to select a different task if the subject perceives a particular task to be the most bothersome. Where two or more tasks have similar amplitudes, Load tasks take priority of Posture tasks and Load-2 task takes priority over Load-1 task. Since Load-2 shows the greatest amplitude and variability, dosing would be based on the data for the Load-2 task. In cases where the amplitude of at least two of the tasks is below the minimum amplitude for inclusion, the clinician must decide whether the joint would be injected at all. The tremor severity is within the inclusion criteria for all the tasks, so the elbow is considered for BoNT A injection.

To select total dose for the elbow based on the Load-2 data from the graph of FIG. 10B, a correlation chart is consulted for the elbow joint. In this case, amplitude is divided into four substantially equal ranges between the proscribed maximum (1.00°) and minimum (0.05°) limits, and dosages are correlated to the four ranges as follows: if total amplitude is 0.77°-1.00° then 60 units; if total amplitude is 0.53°-0.76° then 50 units; if total amplitude is 0.30°-0.52° then 40 units; if total amplitude is 0.05°-0.9° then 0 units. Since the total amplitude of the Load-2 task is in the 0.30°-0.52° range, the total elbow dosage is set at 40 units. Assuming no directional bias, each of M. biceps brachii and M. triceps brachii would receive half of the dosage, i.e. 20 units each. However, since the bicep muscle (M. biceps brachii) is also implicated in supination in the wrist and the elbow data is on verge of being in the 0.53°-0.76° range, a clinician may consider administering a dosage of 50 units to the elbow, 25 units for each of the Bicep and Tricep muscles. But BoNT A dosages are generally given to the shoulder in increments of 10 units, therefore 20 units would be given to the Bicep and 20 units to the Tricep.

Shoulder:

With respect to the shoulder, the upper graph in FIG. 10C shows the amplitude of the tremor at the shoulder in the series of four postural tasks: Post-1, Post-2, Load-1 and Load-2. To determine the amplitude of the tremor, the clinician must first select the postural task or tasks on which to base the determination. The postural task with the highest tremor amplitude or variability is normally selected, although the clinician is free to select a different task if the subject perceives a particular task to be the most bothersome. Where two or more tasks have similar amplitudes, Load tasks take priority of Posture tasks and Load-2 task takes priority over Load-1 task. In the top graph of FIG. 10C, Load-2 is the task to select to determine total amplitude. In cases where the amplitude of at least two of the tasks is below the minimum amplitude for inclusion, the clinician must decide whether the joint would be injected at all. The tremor severity is within the inclusion criteria for all the tasks, so the shoulder is considered for BoNT A injection.

To select total dose for the shoulder based on the Load-2 data from the upper graph of FIG. 10C, a correlation chart is consulted for the shoulder joint. In this case, amplitude is divided into four substantially equal ranges between the proscribed maximum (0.71°) and minimum (0.04°) limits, and dosages are correlated to the four ranges as follows: if total amplitude is 0.55°-0.71° then 80 units; if total amplitude is 0.39°-0.54° then 60 units; if total amplitude is 0.21°-0.38° then 40 units; if total amplitude is 0.04°-0.21° then 0 units. Since the total amplitude of the Load-2 task was close enough to the 0.21°-0.38° range, the total shoulder dosage is set at 40 units.

The lower graph in FIG. 10C shows the contribution of each muscle group to the tremor (i.e. the composition of the tremor) at each postural position, where Shl-Flx refers to the flexor/extensor group and Shl-Abd refers to the abduction/adduction group in the shoulder. To determine how the total dosage is divided between muscle groups, the contribution of each muscle group to the total tremor as shown in the lower graph of FIG. 10C is examined for each task. For Post-1 the contributions are about 45% F/E and 55% Add/Abd. For Post-2 the contributions are about 45% F/E and 55% Add/Abd. For Load-1 the contributions are about 45% F/E and 55% Add/Abd. For Load-2 the contributions are about 47% F/E and 53% Add/Abd. The data from one or more of the tasks is selected, and the selection may be based on the clinicians experience or an average may be taken. In this case, most of the tasks show contributions of each muscle group as 45% F/E and 55% Add/Abd, so this was selected. Since the total dose given to the shoulder is 40 units, the F/E group would receive 18 units and the Add/Abd group would receive 22 units.

In this example the directional bias within a shoulder muscle group is considered to be equal, therefore individual muscles involved in flexion (i.e. M. pectoralis major—see Table 5) would receive half of the dose for the flexor/extensor group, while the individual muscle involved in extension (i.e. M. teres major—see Table 5) would receive the other half. Thus, M. pectoralis major and M. teres major would both receive 9 units of the 18 units determined for the flexor/extensor muscle group. The abductor/adductor muscle group would receive 22 of the total 40 units of BoNT A, with the abductors receiving 11 units and the adductors receiving 11 units given the assumption of no directional bias. There are two abductor muscles in the shoulder (M. deltoideus and M. supraspinatus—see Table 5), so each of these would receive 5.5 units of BoNT A of the 11 units determined for the abductors. There is one adductor muscle in the shoulder (M. pectoralis major—see Table 5), so this muscle would receive the entire 11 units of BoNT A determined for the adductor muscles. Because M. pectoralis major is already receiving 9 units from the dosage determined for flexor muscles, the M. pectoralis major muscle would receive a total of 20 units of BoNT A. Since dosages are given in increments of 5 or 10 units, M. teres major would receive 10 units and M. deltoideus and M. supraspinatus would each receive 5 units.

Summary:

A summary of the dosing on a per-muscle basis is shown in Table 7.

TABLE 7

|  | Wrist | Elbow | Shoulder |
| --- | --- | --- | --- |
| FCR | 5 | | |
| FCU | 5 | | |

TABLE 7-continued

|  | Wrist | Elbow | Shoulder |
|---|---|---|---|
| ECR | 5 | | |
| ECU | 5 | | |
| Sup | 5 | | |
| PQ | 5 | | |
| PT | 5 | | |
| Bicep | | 20 | |
| Tricep | | 20 | |
| Pect Maj | | | 20 |
| Teres Maj | | | 10 |
| M Delt | | | 5 |
| M Supra | | | 5 |
| Total | 35 U | 50 U | 40 U |

The method can provide a series of dosage recommendations for each postural task or generally taking into account all or a subset of the postural tasks. As previously mentioned, a clinician may vary from the recommendation and alter the dosages derived from this method based on other considerations, for example, total dosages may be limited to a maximum amount by regulation, other treatment parameters or affordability, or the drug may be injectable only in set increments (e.g. increments of 5 or 10 units). Further, the correlation of total dosage to tremor severity may be adjusted as more data is collected and the results of treatment evaluated.

For dosing, the task to be considered can be different between joints. If 5 units need to be removed from wrist dosing due to rounding exceeding the desired total dose, then removing 5 units from ECR first is best to minimize risk of spread. If the wrist supinator is injected with greater than or equal to 10 units then the bicep should receive an additional 20 units whether or not tremor severity at the elbow warranted BoNT A injection at the elbow. If the minimum dose to be given to an individual shoulder muscle is set at 20 units and rounding values results in 10 units for Delt and 10 units for Supra, then M Supra should receive 20 units and M Delt should receive 0 units.

Finally, choice of total dosage of BoNT A to be administered to a given joint may be guided by tremor amplitude data as illustrated in this example, or may be simply chosen by a clinician based on past experience or other considerations. However, how that total dosage is divided up between particular muscles can be, and is advantageously, guided by the process described herein to ensure that each muscle receives an appropriate proportion of the total dosage based on that muscle's contribution to the tremor.

Example 5: Determining Botulinum Neurotoxin Type A (BoNT A) Injection Dosages and Muscle Selection Using Data from Kinematic Analysis Kinematic data was collected on the left arm of an essential tremor (ET) subject during a tremor event using the sensor system depicted in FIG. 1. The kinematic data for wrist, shoulder and elbow joints are depicted in FIG. 11A.

To determine the total dosage of Botulinum neurotoxin type A (BoNT A) to inject into muscles of the left arm, Steps 1-12 shown in FIGS. 11B-I are followed. Steps 1-6 in FIGS. 11B-F are for determining BoNT A dosage for wrist muscles. Steps 7-8 in FIG. 11G are for determining BoNT A dosage for elbow muscles. And, Steps 9-12 in FIGS. 11H-I are for determining BoNT A dosage for shoulder muscles FIG. 11J summarizes dosages calculated for the muscles of the left arm of the subject.

The process depicted in FIGS. 11B-I based on the data depicted in FIG. 11A is similar to the process outlined in Example 4. However, in Example 5 raw numerical data derived from sensor data is used instead of data derived from graphs. Further, there is no proscribed upper limit for the dose of BoNT A that may be given to the arm. Dosages of BoNT A are determined solely from the amplitudes of the tremor at the wrist, elbow and shoulder, the amplitudes being compared to respective standard correlation charts (dose tables) for each joint. Each correlation chart provides a maximum BoNT A dose based on the amplitude (severity) of the tremor at the joint. The standard correlation charts were developed from extensive trial and error investigation and informed by the experience of a skilled physician.

As depicted in FIG. 11B, the total dosage of BoNT A to be given to wrist muscles is determined in Steps 1-3 by first determining the amplitude of the tremor for the task where the amplitude is the highest. In this case, the Posture-2 task provides the highest amplitude at 2.26°. From the correlation chart in FIG. 11B, an amplitude of 2.26° corresponds to a total dosage of 80 U to be given to the wrist muscles. To determine how much of the 80 U to give to each muscle group in the wrist, Step 4 as depicted in FIG. 11C utilizes the muscle group composition data for the tremor, the muscle group composition data being provided in FIG. 11A. The total dosage of BoNT A for the wrist is pro-rated for the muscle groups in the wrist in accordance with the contribution of each muscle group to the tremor. To account for directional bias within a muscle group, the wrist bias information in FIG. 11A is utilized in Step 5 depicted in FIGS. 11D-E. The magnitude of the bias in each muscle group is compared to the correlation chart to in FIG. 11D to arrive at the amount by which the dosage will change, and the change will be an increase in dosage for the muscle that the bias favors and a corresponding reduction in dosage for the muscle that the bias does not favor. Thus, the dosage for the muscle group may be divided unequally between the individual muscles in the muscle group if there is a directional bias in the tremor. In this case, all three of the muscle groups (F/E, R/U and P/S) have a directional bias so dosage amounts within the muscle groups are adjusted accordingly as calculated in Steps 5.5-5.6 in FIG. 11E. Exact dosages of BoNT A per wrist muscle are then calculated as shown in Step 6 in FIG. 11F. Because BoNT A dosages are available in specified sizes, the final dosages per muscle are obtained by appropriate rounding of the exact dosages. The total of each of the final dosages should not exceed the total dosage determined from the amplitude (in this case 80 U). Step 6 in FIG. 11F provides steps for reducing dosages at certain muscles in the event the final dosages add up to more than the total dosage determined from the amplitude of the tremor. In this case, the total dosage determined from the amplitude of the tremor and the total of the final dosages are the same so no reductions are required.

As depicted in FIG. 11G, the total dosage of BoNT A to be given to elbow muscles is determined in Step 7 by first determining the amplitude of the tremor for the task where the amplitude is the highest. In this case, the Load-2 task provides the highest amplitude at 0.67°. From the correlation chart in FIG. 11G, an amplitude of 0.67° corresponds to a total dosage of 50 U to be given to the elbow muscles. Step 8 in FIG. 11G illustrates how the total dosage is divided between the elbow muscles. Since there are only two elbow muscles, each muscle received half the total dosage, so each muscle receives 25 U of BoNT A.

As depicted in FIG. 11H, the total dosage of BoNT A to be given to shoulder muscles is determined in Step 9 by first determining the amplitude of the tremor for the task where the amplitude is the highest. In this case, the Load-2 task provides the highest amplitude at 0.34°. From the correlation chart in FIG. 11H, an amplitude of 0.34° corresponds to a total dosage of 60 U to be given to the shoulder muscles. Muscle group contribution to the tremor may then be accounted for in Steps 10-11 in FIG. 11H by multiplying the total dosage by the percentage of contribution for each muscle group, the percentage contribution being provided in the data in FIG. 11A. The exact dose per muscle may then be determined as outlined in Step 12 in FIG. 11I by pro-rating the muscle group contributions to the individual muscles, because certain muscles (e.g. the Pect Maj) may contribute to more than one muscle group. Because BoNT A dosages are available in specified sizes, the final dosages per muscle are obtained by appropriate rounding of the exact dosages. The total of each of the final dosages should not exceed the total dosage determined from the amplitude (in this case 60 U). Step 12 in FIG. 11I provides steps for reducing dosages at certain muscles in the event the final dosages add up to more than the total dosage determined from the amplitude of the tremor. In this case, the total dosage determined from the amplitude of the tremor and the total of the final dosages are the same so no reductions are required.

FIG. 11J provides a summary of the BoNT A dosages to be injected in each of the muscles at each of the joints for the left arm of the Essential Tremor subject from which the data in FIG. 11A was collected. As seen in FIG. 11J, the process has determined that the left arm should receive a total of 190 U of BoNT A, 80 U at the wrist, 50 U at the elbow and 60 U at the shoulder.

Example 6: Dosage Optimization Process

After an initial treatment with Botulinum neurotoxin type A (BoNT A) based on the analyses described above, follow-up treatment of a subject may utilize the injection plan already developed. However, optimization of the injection plan is desirable based on the results obtained with the first treatment. Such an optimization on subject revisits may be determined with the following optimization regimen.
Step 1:
Step 1 involves asking the subject whether the subject has experienced any muscle weaknesses as a result of the first treatment. The question is asked on a per joint basis, preferably starting with the wrist, followed by the elbow and then the shoulder.

1A: If the subject reports a weakness in the wrist, the particular muscle group that is weak is determined. This determination may be done by asking the subject, by examining the subject, by having the subject perform tasks or some combination thereof. If the weakness is flexor-related, the amount of BoNT A injected in the FCR muscle is reduced by 5 units (which may be repeated in serial visits if needed). If the weakness is extensor-related, the amount of BoNT A injected in each of the ECR muscle and ECU muscle is reduced by 5 units (which may be repeated in serial visits if needed). If the weakness is rotation-related, the amount of BoNT A injected in the SUP muscle is reduced by 5 units (which may be repeated in serial visits if needed), and the amount of BoNT A injected in each of the PT muscle and PQ muscle is reduced by 5 units (which may be repeated in serial visits if needed).

1B: If the subject reports a weakness in the elbow, the amount of BoNT A injected in each of the elbow muscles is reduced by 5 units (which may be repeated in serial visits if needed).

1C: If the subject reports a weakness in the shoulder, the particular muscle group that is weak is determined. This determination may be done by asking the subject, by examining the subject, by having the subject perform tasks or some combination thereof. If the weakness is in the Abd/Add group, the amount of BoNT A injected in each of the Abd/Add muscles is reduced by 5 units (which may be repeated in serial visits if needed). If the weakness is in the F/E group, the amount of BoNT A injected in each of the F/E muscles is reduced by 5 units (which may be repeated in serial visits if needed).

In the event a weakness is reported in a joint, then the first treatment regimen is repeated at that joint incorporating the alterations as described above in Step 1. Steps 2 and 3 below are not performed at that joint in the event an alteration to the treatment regimen is undertaken at that joint in accordance with Step 1. Where a weakness is reported in one joint, but not in other joints, Step 1 may be performed on the joint affected by the weakness but Step 2 or 3 may be performed on the joint or joints not affected by the weakness.
Step 2:
In the event that no weakness to a joint is reported in Step 1, then another set of kinematic measurements are taken at each of the joints involved in the tremor for which no weakness was reported in Step 1. In taking the measurements, tremor amplitude is determined from the task where the tremor amplitude is the greatest.

2A: If the tremor amplitude (severity) at the newly measured joints has reduced to an acceptable level according to the new data, then proceed to Step 3 below for those joints.

2B: If the tremor amplitude (severity) at the newly measured joints has not reduced enough and there is a shift of 10% or more in the contributions from each muscle group compared to the previous assessment, then 10 units of BoNT A are added to the muscle group that has the dominant effect in the tremor. The amount of BoNT A injected in the other muscle groups is not reduced.

2C: If contributions have less than a 10% shift compared to previous assessment, then all muscle groups receive 5 units of BoNT A.

If Step 2 requires an adjustment to the BoNT A injection at a joint as described above, then do not proceed to Step 3 for that joint.
Step 3:
If a treatment adjustment at a joint is undertaken in accordance with Step 1 or Step 2, then Step 3 is not performed for the joints that underwent the treatment adjustment. If a treatment adjustment at a joint is not undertaken in accordance with Step 1 or Step 2, then Step 3 is performed for the joints that did not undergo the treatment adjustment.

In Step 3, the subject is asked whether the tremor at the particular joint in question is better. This question is asked despite no weakness reported in Step 1 and an improvement determined in Step 2. Sometimes the subject may have been generally experiencing little or no improvement over the course of time, while the measurements in Step 2 may have been on a day where the tremor just happened to be not as severe as usual.

3A: If the subject reports that the tremor is better, then no changes to the treatment are made and the subject is treated with a repeat of the first treatment regimen.

3B: If the subject reports that the tremor is not better but cannot identify a specific movement that causes the most tremor, then the BoNT A dosage at each muscle that was previously dosed is increased by 5 units but no BoNT A is injected into muscles that did not previously receive BoNT A. Each joint is assessed independently.

3C: If the subject reports that the tremor is flexor-related, the amount of BoNT A injected in the FCR and FCU muscle is increased by 5 units (which may be repeated in serial visits if needed). If the tremor is extensor-related, the amount of BoNT A injected in each of the ECR muscle and ECU muscle is increased by 5 units (which may be repeated in serial visits if needed). If the weakness is rotation-related, the amount of BoNT A injected in the SUP muscle is increased by 5 units (which may be repeated in serial visits if needed), and the amount of BoNT A injected in each of the PT muscle and PQ muscle is increased by 5 units (which may be repeated in serial visits if needed). If the tremor is radial related, the amount of BoNT A injected in each of the FCR muscle and ECR muscle is increased by 5 units (which may be repeated in serial visits if needed).

3D: If the subject reports a tremor in the elbow, the amount of BoNT A injected in each of the elbow muscles is increased by 5 units (which may be repeated in serial visits if needed).

3E: If the subject reports a tremor in the shoulder, the particular muscle group that is causing tremor is determined. This determination may be done by asking the subject, by examining the subject, by having the subject perform tasks or some combination thereof. If the tremor is in the Abd/Add group, the amount of BoNT A injected in each of the Abd/Add muscles is increased by 5 units (which may be repeated in serial visits if needed). If the tremor is in the F/E group, the amount of BoNT A injected in each of the F/E muscles is increased by 5 units (which may be repeated in serial visits if needed).

References: The contents of the entirety of each of which are incorporated by this reference.

Benito-Leon J, Louis E D. (2011) "Update on essential tremor." *Minerva Med.* 102, 417-40.

Deuschl G, et al. (1998) "Consensus statement of the Movement Disorder Society on Tremor. Ad Hoc Scientific Committee." *Mov Disord.* 13, Suppl 3, 2-23.

Fahn S, et al. (2003) "Clinical rating scale for tremor." in *Parkinson's disease and movement disorders*. J. Jankovic and E. Tolosa, Eds., ed: Williams and Wilkins, 1993.

Rahimi F, et al. (2011) "Variability of hand tremor in rest and in posture—a pilot study." in *Conf Proc IEEE Eng Med Biol Soc.* 470-3.

Rahimi F, Bee C, Debicki D, Roberts A C, Bapat P, Jog M. (2013) Effectiveness of BoNT A in Parkinson's Disease Upper Limb Tremor Management. *Can J Neurol Sci.* 40, 663-669.

The novel features of the present invention will become apparent to those of skill in the art upon examination of the detailed description of the invention. It should be understood, however, that the scope of the claims should not be limited by the preferred embodiments set forth in the examples, but should be given the broadest interpretation consistent with the specification as a whole.

The invention claimed is:

1. A system for providing a dosage recommendation for treating a movement disorder with a drug in a subject, the system comprising:
    a plurality of kinematic sensors configured to be placed on a body of a subject experiencing a movement disorder proximal a plurality of joints of the subject, the kinematic sensors selected to measure overall joint motion with degrees of freedom for individual joints so that data collected by the sensors can be deconstructed into multiple degrees of freedom for individual joints and analyzed to provide amplitude of the movements caused by the movement disorder, and relative contributions from and directional bias for each muscle group that may be implicated in the movement of each joint; and,
    a non-transient, physical memory device configured to accept data collected by the kinematic sensors and having computer executable instructions stored thereon to deconstruct the data collected by the sensors for overall joint motion into multiple degrees of freedom for individual joints and analyzing the multiple degrees of freedom for the amplitude of the movements caused by the movement disorder and the relative contributions from and directional bias for each muscle group that may be implicated in the movement of each joint,
    wherein for a given joint, the computer executable instructions:
        further determine from the amplitude of the movements a total dosage of the drug to administer to the muscles implicated in the movements at the joint;
        further determine from the relative contributions of each muscle group a proportion of the total dosage to administer to each muscle group implicated in the movements at the joint;
        further determine from the directional bias a proportion of the dosage to be administered to each muscle group to administer to each individual muscle in the muscle group; and,
        calculate from the total dosage and each determined proportion the dosage of the drug to administer to each individual muscle implicated in the movement of the joint.

2. The system according to claim 1, wherein the plurality of kinematic sensors comprises at least one goniometer.

3. The system according to claim 1, wherein the plurality of kinematic sensors comprises at least one accelerometer, at least one gyroscope and at least one electromagnetometer.

4. The system according to claim 1, wherein the movement disorder comprises tremor.

5. The system according to claim 1, wherein the movement disorder is Parkinson's disease (PD) or essential tremor (ET).

6. The system according to claim 1, wherein the movement disorder comprises spasticity or dystonia.

7. The system according to claim 1, wherein the movement disorder comprises focal spasticity from stroke.

8. The system according to claim 1, wherein the movement disorder comprises multiple sclerosis.

9. The system according to claim 1, wherein the muscle groups comprise muscles in upper limbs of the subject.

10. The system according to claim 1, wherein the muscle groups comprise one or more of abduction/adduction (NA) muscles, flexion-extensor (F/E) muscles, ulnar-radial (U/R) muscles and pronation-supination (P/S) muscles.

11. The system according to claim 1, wherein the computer executable instructions compare the amplitude of the movement of each individual joint to a standard curve of amplitude vs. total dosage or to a standard dosage for a range of amplitudes to determine a total dosage of the drug to be administered to each individual joint.

* * * * *